US009322782B2

(12) United States Patent
Kishima

(10) Patent No.: US 9,322,782 B2
(45) Date of Patent: Apr. 26, 2016

(54) IMAGE OBTAINING UNIT AND IMAGE OBTAINING METHOD

(71) Applicant: Sony Corporation, Tokyo (JP)

(72) Inventor: Koichiro Kishima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 50 days.

(21) Appl. No.: 14/059,791

(22) Filed: Oct. 22, 2013

(65) Prior Publication Data
US 2014/0131592 A1    May 15, 2014

(30) Foreign Application Priority Data

Nov. 13, 2012    (JP) ................................. 2012-249208

(51) Int. Cl.
*G01J 1/00*    (2006.01)
*G01N 21/64*    (2006.01)
(52) U.S. Cl.
CPC ........ *G01N 21/6428* (2013.01); *G01N 21/6458* (2013.01)
(58) Field of Classification Search
CPC .......... G01N 21/6428; G01N 21/6458; G01N 21/64; G01N 21/6408; G01N 2021/6421
USPC ...................................................... 250/459.1
See application file for complete search history.

(56) References Cited

U.S. PATENT DOCUMENTS

| 2011/0122250 A1* | 5/2011 | Lee et al. ........................ 348/155 |
| 2011/0194175 A1* | 8/2011 | Dougherty et al. ........... 359/386 |
| 2011/0216182 A1* | 9/2011 | Kishima ........................ 348/79 |
| 2012/0002032 A1* | 1/2012 | Narusawa et al. ............... 348/79 |
| 2013/0093871 A1* | 4/2013 | Nowatzyk et al. .............. 348/79 |
| 2014/0125776 A1* | 5/2014 | Damaskinos et al. .......... 348/50 |

FOREIGN PATENT DOCUMENTS

JP    2011-107669    6/2011

OTHER PUBLICATIONS

HER2 testing guidelines, third edition, created by Trastuzumab pathology committee, Sep. 2009, p. 10 <Fish-method determination method> (30 pages).

* cited by examiner

*Primary Examiner* — David Porta
*Assistant Examiner* — Mamadou Faye
(74) *Attorney, Agent, or Firm* — Hazuki International, LLC

(57) ABSTRACT

An image obtaining apparatus and an image obtaining method are provided. The image obtaining apparatus including a light source configured to generate excitation light causing a fluorescent label of a biological sample to emit light; an image sensor; an optical system configured to cause the image sensor to form a fluorescent image of the partial area of the biological sample; a movement control unit; a generation unit configured to continuously expose the image sensor during the movement of the focal position of the optical system, and to generate a long-time exposed image of the partial area; and a calculation unit configured to analyze a frequency of the generated long-time exposed image, and to calculate positional information in the optical axis direction of the fluorescent label by using at least results of the analysis.

8 Claims, 17 Drawing Sheets

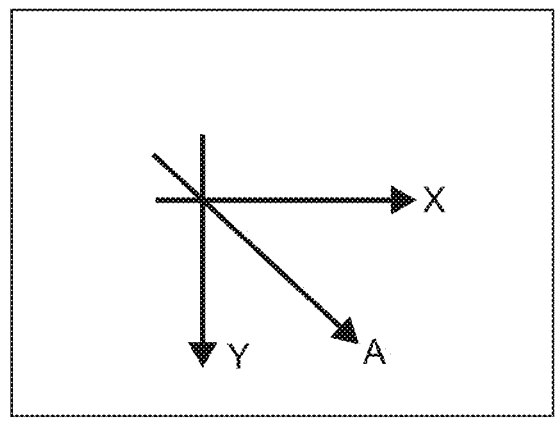
FIG.19
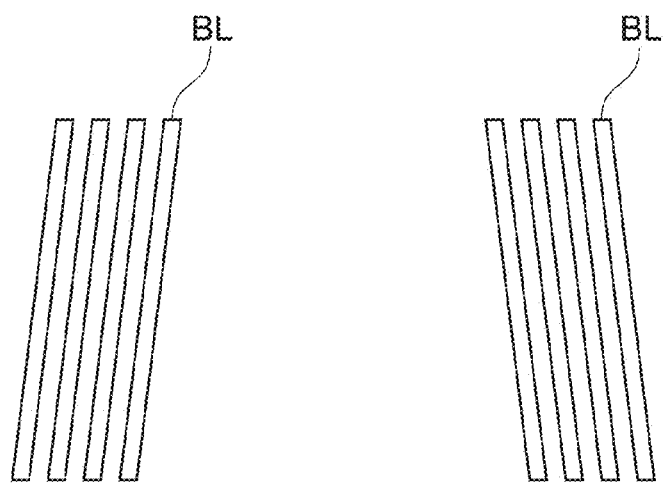
Pattern A          Pattern B
FIG.20
FIG.21A
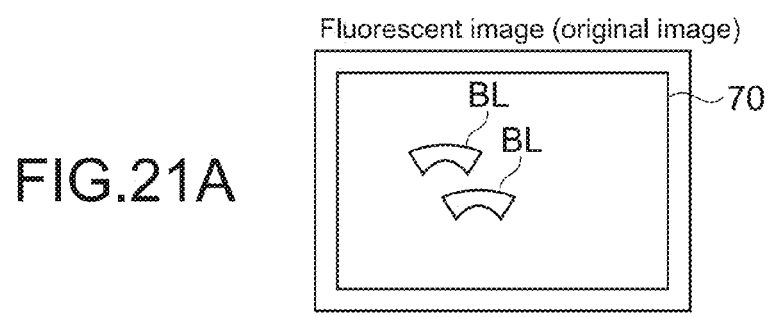

Image obtained by displacing original image by predetermined number of pixels to left direction FIG.21B
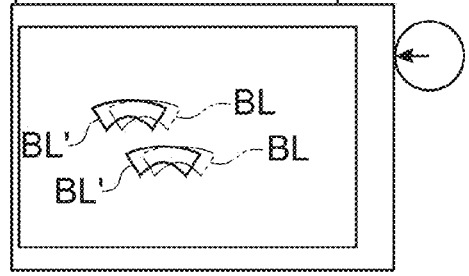

Image obtained by displacing original image by predetermined number of pixels to lower left direction FIG.21C
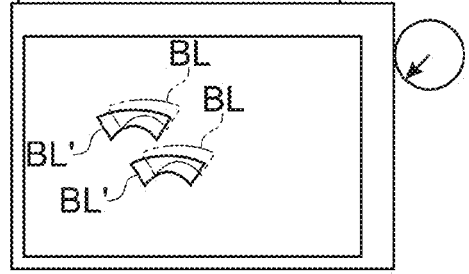

Image obtained by displacing original image by predetermined number of pixels to downward direction FIG.21D
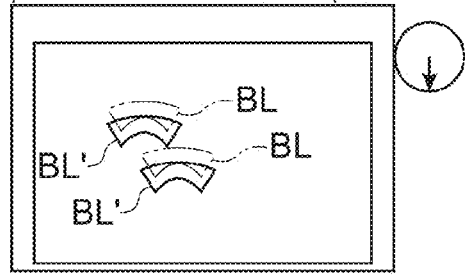

Image obtained by displacing original image by predetermined number of pixels to lower right direction FIG.21E
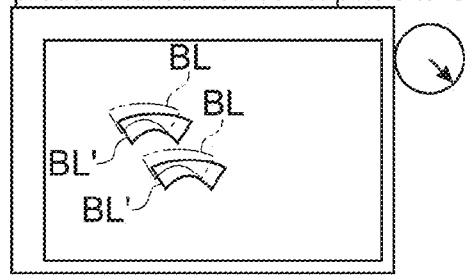

IMAGE OBTAINING UNIT AND IMAGE OBTAINING METHOD

CROSS REFERENCES TO RELATED APPLICATIONS

The present application claims priority to Japanese Priority Patent Application JP 2012-249208 filed in the Japan Patent Office on Nov. 13, 2012, the entire content of which is hereby incorporated by reference.

BACKGROUND

The present disclosure relates to an image obtaining apparatus and an image obtaining method, which obtain an image using a microscope.

A method of analyzing a tissue slice removed in surgery and selecting a medication administered to a patient after surgery based on the analysis results has been used in the past in treatment for a breast cancer, for example.

For example, a HER-2DNA probe kit manufactured by ABBOTT JAPAN CO., LTD is used to fluorescence-stain a tissue slice removed in surgery. If excitation light is applied to the tissue slice, fluorescence of red is generated from a HER2/neu gene, and fluorescence of green is generated from an alpha satellite DNA sequence. Therefore, the HER2/neu gene is labeled by a bright spot of red, and the alpha satellite DNA sequence is labeled by a bright spot of green.

In diagnosis using a fluorescent microscope, the numbers of bright spots of red and bright spots of green are counted. Then, if the number of bright spots of red is more than 2.2 times that of bright spots of green, it is determined to be a positive-HER2 reaction. In this case, it is said that the prognosis of a patient after surgery is significantly improved by administering a molecular targeted agent, Herceptin (registered trademark) manufactured by F. Hoffmann-La Roche, Ltd (see, HER2 testing guidelines, third edition, created by Trastuzumab pathology committee, September, 2009, p. 10 <Fish-method determination method>).

Moreover, Japanese Patent Application Laid-open No. 2011-107669 discloses a technique to detect bright spots that label cells from a fluorescent image of a biological sample. In the biological sample image obtaining apparatus disclosed in Japanese Patent Application Laid-open No. 2011-107669, the target part of the biological sample is magnified by an objective lens and is photographed. The accuracy of detecting bright spots is improved by moving the focal point of the objective lens as appropriate during the photographing.

SUMMARY

In the diagnostic using a microscope described above or the like, it is important to appropriately set a focal position of an optical system. For example, a sample such as a tissue slice is placed on a glass slide, and a cover glass is put thereon via a mounting agent. The prepared slide thus created is set on a stage of the fluorescent microscope. At this time, there is a need to adjust the focal position for each prepared slide placed on the stage due to various reasons such as the uneven thickness of the sample, the uneven thickness of the glass slide, and the dust sandwiched between the glass slide and the stage.

On the other hand, the resolution of an image observed by the fluorescent microscope and the brightness of bright spots are increased as the numerical aperture (NA) of the optical system is increased. Therefore, with a microscope using an optical system having higher numerical aperture (NA), the accuracy of the diagnosis tends to be increased. However, if the numerical aperture (NA) of the optical system is increased, the focal position is easy to be missed because the focal depth is decreased. Specifically, the above-mentioned adjustment of the focal point is difficult to perform.

In view of the above, for example, a method of searching for a focal position by taking an image every time the focal position is changed at an interval smaller than the focal depth, and analyzing the taken image is conceivable. However, the method needs to take a lot of images, and needs a high-capacity memory for storing data in the amount of the taken images. Moreover, because the method needs to refer to data of a plurality of images in order to calculate a focal position, it takes a lot of man-hours and is inefficient. As described above, it is inefficient to take an image by using a fluorescent microscope in some cases, and therefore improvement is necessary in various aspects.

In view of the circumstances as described above, it is desirable to provide an image obtaining apparatus and an image obtaining method, which are capable of efficiently taking an image of a biological sample to which a fluorescent label is attached.

(1) According to an embodiment of the present disclosure, there is provided an image obtaining apparatus, including a light source configured to generate excitation light causing a fluorescent label of a biological sample to emit light, an image sensor configured to form an image, an optical system configured to apply the excitation light from the light source to at least a partial area of the biological sample, the part including the fluorescent label, and to cause the image sensor to form a fluorescent image of the partial area, a movement control unit configured to move a focal position of the optical system to an optical axis direction of the optical system and a direction perpendicular to the optical axis, a generation unit configured to continuously expose the image sensor during the movement of the focal position of the optical system, and to generate a long-time exposed image of the partial area, and a calculation unit configured to analyze a frequency of the generated long-time exposed image, and to calculate positional information in the optical axis direction of the fluorescent label by using at least results of the analysis.

In the embodiment of the present disclosure, a frequency of a long-time exposed image is analyzed, positional information of a fluorescent label in an optical axis direction is calculated based on at least results of the analysis, and a fluorescent image for diagnosis is taken based on the calculated positional information. Therefore, it is possible to efficiently take an image of a biological sample to which a fluorescent label is attached.

(2) In the image obtaining apparatus, the calculation unit may analyze a frequency of the long-time exposed image in at least one direction different from two directions set in advance, the two directions being perpendicular to each other, determine one of the directions, which has the highest frequency component, and calculate the positional information based on the determined direction.

In the embodiment of the present disclosure, because a frequency of a long-time exposed image is analyzed in at least three directions, it is possible to accurately determine one direction, which has the highest maximum frequency component, out of the at least three directions.

(3) In the image obtaining apparatus, the calculation unit may store information on correlation between the directions to be determined and the positional information in advance, and calculate the positional information from the determined direction based on the information on correlation.

In the embodiment of the present disclosure, information on correlation between directions to be determined and positional information is stored in advance, and a process is performed based on the information on correlation. Therefore, it is possible to appropriately calculate positional information even if a focal position of an optical system is not moved at a constant speed when a long-time exposed image is taken.

(4) In the image obtaining apparatus, the calculation unit may generate a moving image obtained by moving the long-time exposed image by the number of pixels set in advance for each direction, obtain a correlation between the long-time exposed image and each moving image, and determine one of the directions, which has the lowest correlation.

In the embodiment of the present disclosure, it is possible to determine one direction, which has the lowest correlation, by only a simple process of moving an image and calculating a correlation coefficient by using a difference from an original image, for example.

(5) According to an embodiment of the present disclosure, there is provided an image obtaining method, including generating excitation light causing a fluorescent label of a biological sample to emit light, applying the excitation light to at least a partial area of the biological sample, the part including the fluorescent label, and causing an image sensor to form a fluorescent image of the partial area by an optical system, moving a focal position of the optical system to an optical axis direction of the optical system and a direction perpendicular to the optical axis, continuously exposing the image sensor during the movement of the focal position of the optical system, and generating a long-time exposed image of the partial area, and analyzing a frequency of the generated long-time exposed image, and calculating positional information in the optical axis direction of the fluorescent label by using at least results of the analysis.

As described above, according to the present disclosure, it is possible to efficiently take an image of a biological sample to which a fluorescent label is attached.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIG. 19 is a diagram in which an x-axis direction being a horizontal direction of a fluorescent image, a y-axis direction being a vertical direction of the fluorescent image, and a direction A inclined by 45 degrees with respect to the X- and y-axis directions are determined as directions for obtaining a frequency component;

FIG. 20 is a diagram showing a state where a brightest and nearly straight portion BL of the locus of bright spots appears in two directions;

FIG. 21A is a diagram showing a fluorescent image being an original image that is not displaced;

FIG. 21B is a diagram showing a state where a correlation between the original image and an image obtained by displacing the original image by the predetermined number of pixels to the left direction is obtained;

FIG. 21C is a diagram showing a state where a correlation between the original image and an image obtained by displacing the original image by the predetermined number of pixels to the lower left direction is obtained;

FIG. 21D is a diagram showing a state where a correlation between the original image and an image obtained by displacing the original image by the predetermined number of pixels to the downward direction is obtained;

FIG. 21E is a diagram showing a state where a correlation between the original image and an image obtained by displacing the original image by the predetermined number of pixels to the lower right direction is obtained.

DETAILED DESCRIPTION

Figure 1:
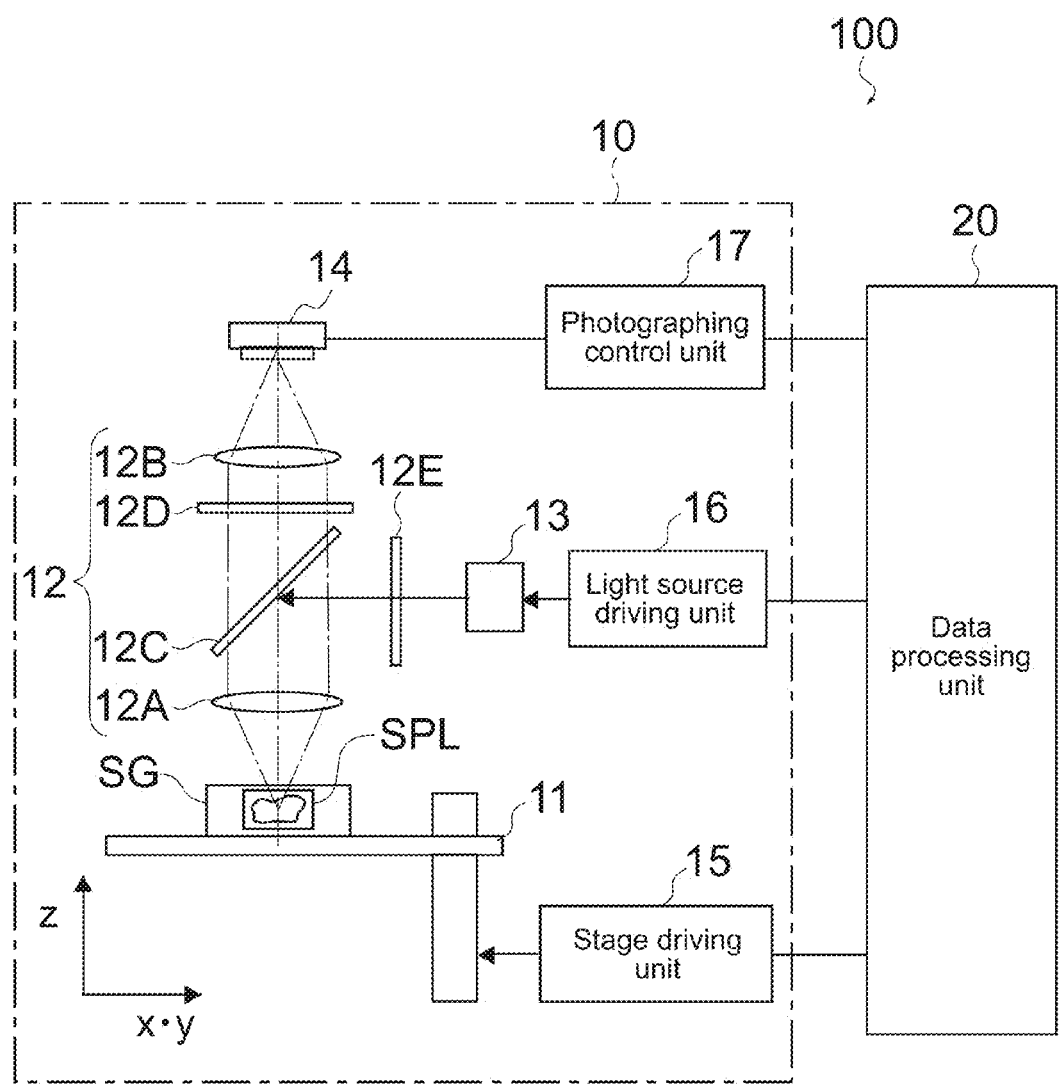
FIG. 1 is a schematic diagram showing an image obtaining apparatus according to an embodiment of the present disclosure.

Hereinafter, an embodiment of the present disclosure will be described with reference to the drawings.

In the present disclosure, when a fluorescent microscope takes a fluorescent image of a prepared slide prepared by staining a tissue collected from a living body by a fluorescent marker (hereinafter, referred to as biological sample SPL), the fluorescent microscope automatically focuses on an appropriate position.

In the following description, taking a fluorescent image for diagnosis with appropriately focusing on a bright sport of a fluorescent marker in the biological sample SPL is referred to as "actual photographing," and taking a fluorescent image for adjusting a focal position for searching for an appropriate focal position, which is performed prior to the "actual photographing" for the "actual photographing," is referred to as "preliminary photographing." The present disclosure relates to the preliminary photographing. It should be noted that because the actual photographing is typical photographing using a fluorescent microscope, the description thereof will be omitted.

It should be noted that in the case where the present disclosure is applied to the preliminary photographing using a fluorescent microscope, the application method is partly different depending on how a tissue is collected from a living body. For example, in the case where the sample is one collected in a blood test or a urinary test, if an image of the completed biological sample SPL is taken, the density of cells or bright spots fluorescence-stained in the cells in a taken image is low, and the numbers thereof are individually different, e.g., range from several to about a hundred.

On the other hand, in the case of the biological sample SPL prepared from a sample such as organs obtained as a slice removed in surgery, the cell density is high, and the number of bright spots in a taken image is not less than several hundreds. Therefore, in the case where cell nuclei are fluorescence-stained, it is not easy to separately observe the individual cell nuclei.

In the following description, the application of the present disclosure specialized for the case where an image of the biological sample SPL having a low cell density and a few bright spots is taken is described in detail in a first embodiment of the present disclosure, and the application of the present disclosure including states having a low cell density and a high cell density is described in a second embodiment of the present disclosure.

It should be noted that in the following description, it is assumed that the density of a bright spot is low if the cell density is low, and the density of a bright spot is high if the cell density is high. If the cell density is high and the density of a bright spot is low, the actual photographing may be performed by the method according to the first embodiment in which the cell density is assumed to be low.

First Embodiment

In a first embodiment of the present disclosure, a state where the cell density in the biological sample SPL photographed by a fluorescent microscope is low, and individual bright spots of a fluorescent image obtained by staining the cells by a fluorescent label are clearly identified is assumed. Therefore, a feature of the present disclosure in the first embodiment is to clearly identify individual bright spots of a fluorescent image, and to analyze the shape of each bright spot.

[Regarding Configuration of Image Obtaining Apparatus]

The configuration of an image obtaining apparatus that performs the preliminary photographing and the actual photographing in this embodiment will be described first. FIG. 1 is a schematic diagram showing an image obtaining apparatus according to an embodiment of the present disclosure. As shown in FIG. 1, an image obtaining apparatus 100 according to this embodiment includes a microscope 10 and a data processing unit 20. Hereinafter, the configurations of the microscope 10 and the data processing unit 20 will be described in detail.

[Regarding Configuration of Microscope 10]

The microscope 10 includes a stage 11, an optical system 12, a light source 13, and an image sensor 14. The stage 11 includes a placing surface on which the biological sample SPL such as a tissue slice, a cell, and a biopolymer including a chromosome, can be placed, and can be moved in a direction parallel to the placing surface (x-y plane direction) and a direction perpendicular to the placing surface (z-axis direction).

The direction perpendicular to the placing surface (z-axis direction) corresponds to the thickness direction of the biological sample SPL. The direction parallel to the placing surface (x-y plane direction) corresponds to a plane direction perpendicular to the thickness direction.

The optical system 12 is disposed above the stage 11. The optical system 12 includes an objective lens 12A, an imaging lens 12B, a dichroic mirror 12C, an emission filter 12D, and an excitation filter 12E. The light source 13 includes, for example, a light bulb such as a silver lump or an LED (Light Emitting Diode), and applies excitation light to a fluorescent label attached to the biological sample SPL.

When obtaining a fluorescent image of the biological sample SPL, the excitation filter 12E generates excitation light by transmitting only light having the excitation wavelength of exciting a fluorochrome out of light emitted from the light source 13. The dichroic mirror 12C reflects the excitation light incident by being transmitted through the excitation filter to the objective lens 12A. The objective lens 12A collects the excitation light to the biological sample SPL. Then, the objective lens 12A and the imaging lens 12B magnify the image of the biological sample SPL at a predetermined magnification, and cause the magnified image to be imaged on the imaging surface of the image sensor 14.

If the excitation light is applied to the biological sample SPL, stains bonded to the tissues of the biological sample SPL emit fluorescence. The fluorescence is transmitted through the dichroic mirror 12C via the objective lens 12A, and reaches the imaging lens 12B via the emission filter 12D. The emission filter 12D absorbs the light magnified by the objective lens 12A and transmitted through the excitation filter 12E, and causes only a part of the color-producing light to be transmitted therethrough. An image of the color-producing light having lost outside light is magnified by the imaging lens 12B and is imaged on the image sensor 14, as described above.

As the imaging sensor 14, for example, a CCD (Charge Coupled Device) or CMOS (Complementary Metal Oxide Semiconductor) image sensor is used. The image sensor 14 includes a photoelectric conversion element that receives light by colors of RGB (Red, Green, and Blue) and converts the light into an electric signal, and is a color imager that obtains a color image from incident light.

[Regarding Biological Sample SPL Placed on Stage 11 and Bright Spot]

Figure 2:
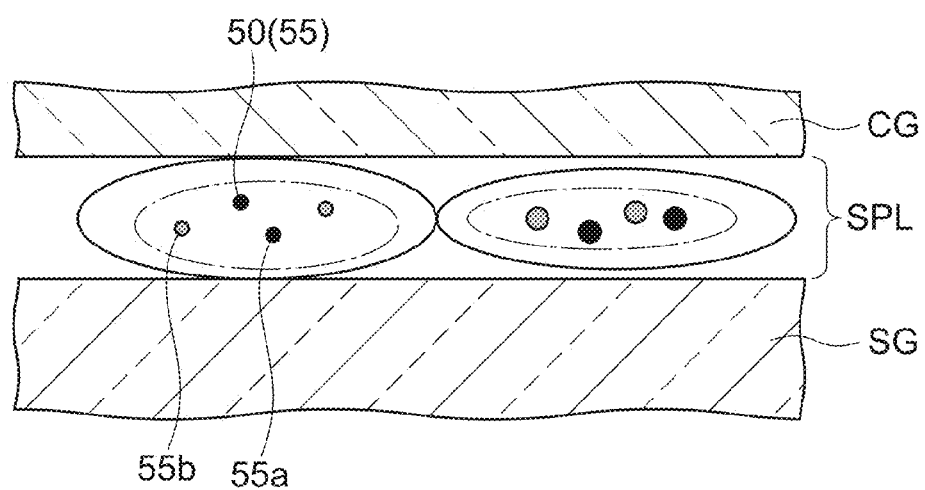
FIG. 2 is a diagram showing a biological sample placed on a stage 11 from a lateral direction.

FIG. 2 is a diagram showing the biological sample SPL (prepared slide) placed on the stage 11 from a lateral direction of the stage 11. As shown in FIG. 2, the biological sample SPL has a thickness of, for example, several µm to several 10 µm in the z direction. Moreover, the biological sample SPL is sandwiched between a glass slide SG and a cover glass CG, and is fixed by a predetermined fixing method. The thickness of the glass slide SG is, for example, about 1 mm. The thickness of the cover glass CG is, for example, about 0.15 to 0.17 mm.

The biological sample SPL is stained with a fluorescence stain. The fluorescence stain is a stain that emits fluorescence by excitation light applied from the same light source. Examples of the fluorescence stain include DAPI (4',6-diamidino-2-phenylindole), SpAqua, and SpGreen.

The biological sample SPL is stained, and thus a fluorescent label is attached to a target biological tissue 50 in the biological sample SPL. If predetermined excitation light is applied to the fluorescent label, predetermined fluorescence is emitted from the fluorescent label. Therefore, in the case where a fluorescent image is generated by taking an image of the biological sample SPL, the target biological tissue 50 is labeled by a bright spot showing a predetermined color (hereinafter referred to as "fluorescent marker 55").

[Regarding Configuration of Data Processing Unit]

The data processing unit 20 drives the light source 13, obtains a fluorescent image of the biological sample SPL by using the image sensor 14, and stores the fluorescent image as sample data.

Figure 3:
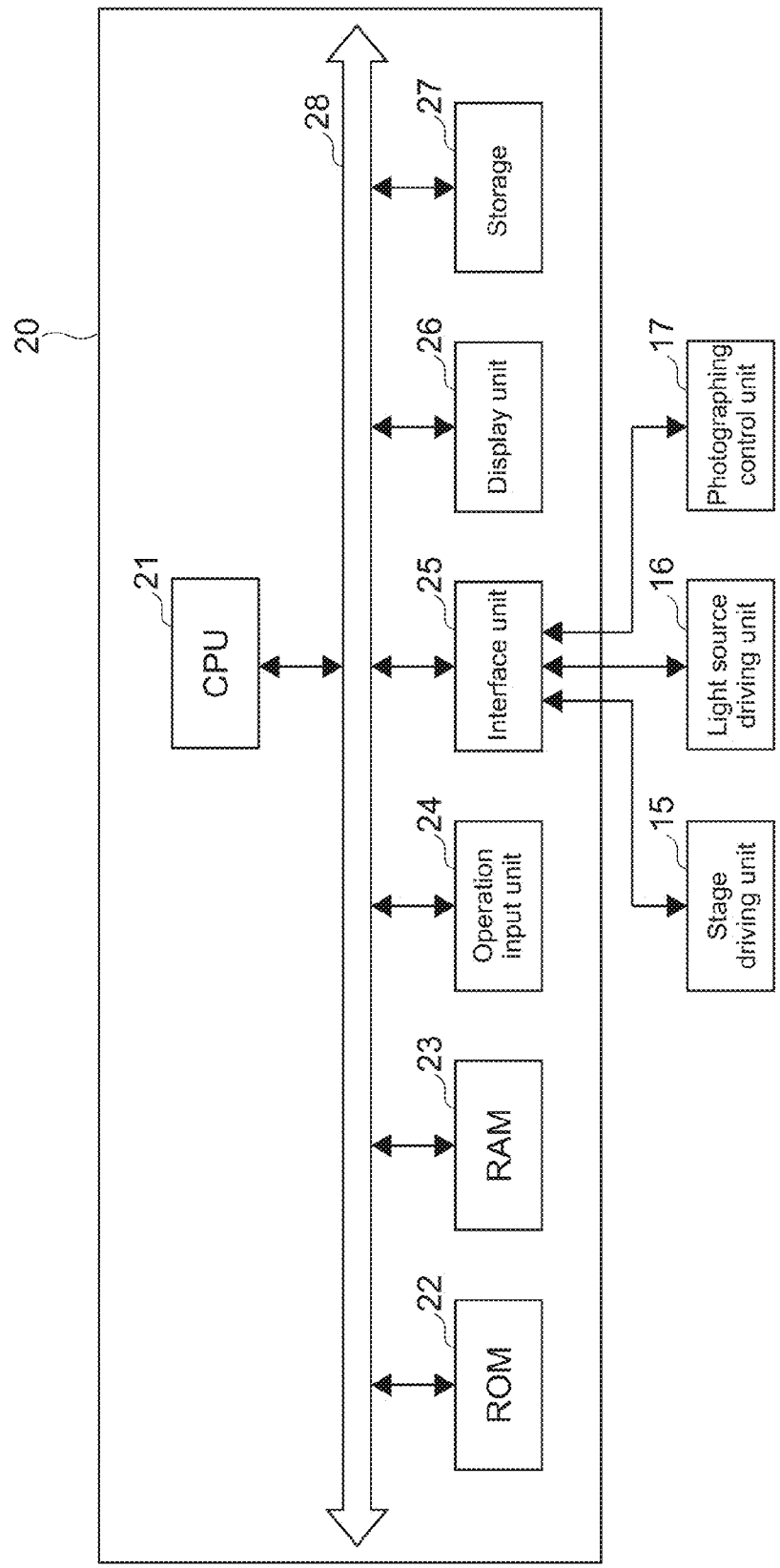
FIG. 3 is a block diagram showing the hardware configuration of a data processing unit 20.

FIG. 3 is a block diagram showing the hardware configuration of the data processing unit 20. The data processing unit 20 includes a computer such as a PC (Personal Computer). The data processing unit 20 stores a fluorescent image of the biological sample SPL obtained by the image sensor 14 as digital image data in an arbitrary format such as JPEG (Joint Photographic Experts Group).

As shown in FIG. 3, the data processing unit 20 includes a CPU (Central Processing Unit) 21, a ROM (Read Only Memory) 22, a RAM (Random Access Memory) 23, an operation input unit 24, an interface unit 25, a display unit 26, and a storage 27, and the blocks are connected via a bus 28.

The ROM 22 fixedly stores a plurality of programs such as firmware for executing various processes and data. The RAM 23 is used as a work area of the CPU 21, and temporarily stores an OS (Operating System), various applications being executed, and various types of data being processed.

The storage 27 includes, for example, an HDD (Hard Disk Drive), a flash memory, or another non-volatile memory such as a solid-state memory. The storage 27 stores an OS, various applications, and various types of data. In this embodiment, particularly, the storage 27 stores also fluorescent image data captured from the image sensor 14 or an image processing application that performs the image process of the fluorescent image data.

The interface unit 25 is connected to control substrates (stage driving unit 15, light source driving unit 16, and photographing control unit 17), which drive the stage 11 of the microscope 10, the light source 13, and the image sensor 14, respectively, and exchange signals between the control substrates and the data processing unit 20 by predetermined communication standards.

The CPU 21 expands a program corresponding to a command given from the operation input unit 24 into the RAM 23 out of the plurality of programs stored in the ROM 22 or the storage 27, and controls the display unit 26 and the storage 27 according to the expanded program as appropriate.

The operation input unit 24 includes an operation apparatus such as a pointing device including a mouse, a key board, and a touch panel.

The display unit 26 includes, for example, a liquid crystal display, an EL (Electro-Luminescence) display, a plasma display, or a CRT (Cathode Ray Tube) display. The display unit 26 may be incorporated in the data processing unit 20 or externally connected to the data processing unit 20.

[Regarding Overview of Process of Obtaining Image of Biological Sample (Preliminary Photographing)]

In this embodiment, in order to search for a focal position for the actual photographing, the focal position of the optical system 12 is moved in the photographing range including the thickness of a portion to be photographed of the biological sample SPL in the preliminary photographing. The image sensor 14 is exposed during the movement of the focal position, and thus a preliminary photographing fluorescent image of the biological sample SPL is obtained. Based on the preliminary photographing fluorescent image, distribution information of the fluorescent label in the thickness direction of the photographing target is calculated. The distribution information of the fluorescent label corresponds to distribution information of the target biological tissue 50 labeled by the fluorescent marker 55.

Based on the calculated distribution information, it is possible to easily calculate a focal position for taking an image of the fluorescent marker 55 as appropriate, for example. As a result, it is possible to efficiently take an image of the biological sample SPL to which the fluorescent marker 55 is attached. Hereinafter, the description thereof will be made in detail.

[Regarding Functional Block of Process of Obtaining Image of Biological Sample (Preliminary Photographing)]

The CPU 21 of the data processing unit 20 expands a program corresponding to a command given from the operation input unit 24 into the RAM 23 out of the plurality of programs stored in the ROM 22 or the storage 27. The CPU 21 executes a process of obtaining an image of a biological sample based on the expanded program (image obtaining program).

Figure 4:
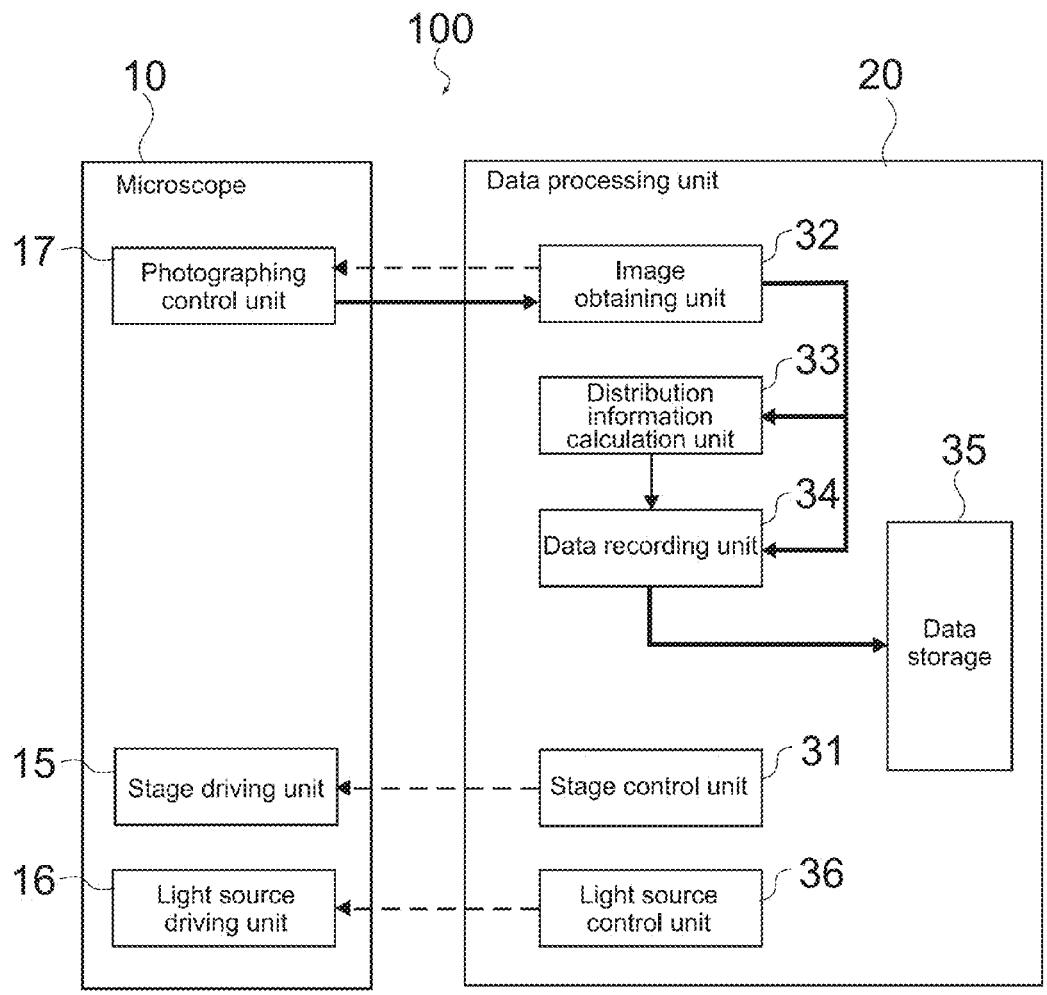
FIG. 4 is a functional block diagram for a process of obtaining an image of a biological sample according to this embodiment.

FIG. 4 is a functional block diagram for the process of obtaining the image of the biological sample. The data processing unit 20 includes a stage control unit 31 (movement control unit), an image obtaining unit 32 (generation unit), a distribution information calculation unit 33 (calculation unit), a data recording unit 34, a data storage 35, and a light source control unit 36.

Figure 5:
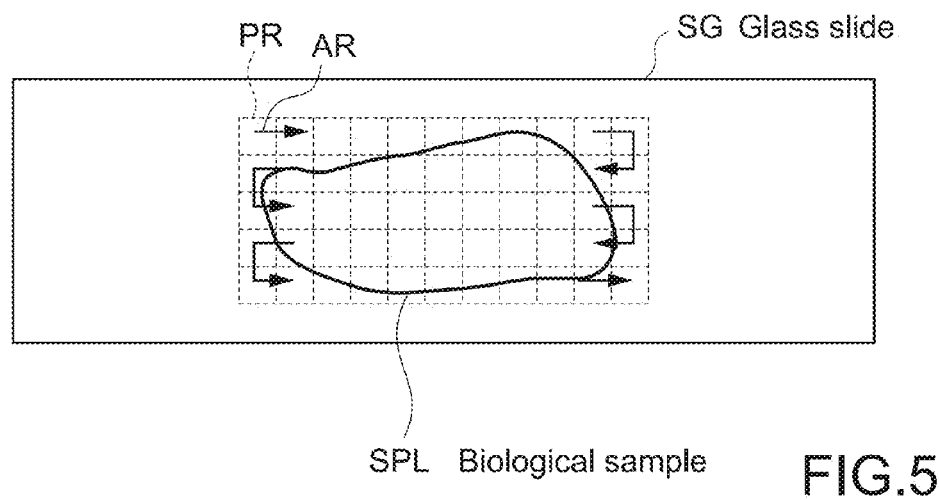
FIG. 5 is a diagram showing an area of which an image is taken by an image obtaining apparatus.

The stage control unit 31 sequentially moves the stage 11 so that a part to be photographed of the biological sample SPL (hereinafter, referred to also as sample part) is positioned in the photographing range, and allocates the biological sample SPL in photographing ranges AR as shown in FIG. 5, for example. It should be noted that in FIG. 5, although areas of the biological sample SPL to be allocated in the photographing ranges AR are not overlapped, a part of adjacent areas may be overlapped.

Moreover, the stage control unit 31 integrally and simultaneously moves the stage 11 in the x-axis direction, the y-axis direction, and the z-axis direction while exposing the image sensor 14 in order to take a fluorescent image for adjusting a focal position. The integrative movement method will be described later.

The image obtaining unit 32 sends a command of exposing the sensor image 14 to the photographing control unit 17 in order to take a fluorescent image for adjusting a focal position every time the target sample part is moved in the photographing range AR by the movement of the stage 11.

The image obtaining unit 32 obtains a fluorescent image for adjusting a focal position of the sample part from the image sensor 14 via the photographing control unit 17 every time the photographing of a fluorescent image for adjusting a focal position is finished. Then, the image obtaining unit 32 generates an image of the whole biological sample by coupling images of the sample part to be allocated in the photographing ranges AR using a predetermined coupling algorithm.

The distribution information calculation unit 33 calculates distribution information of the fluorescent marker 55 in the thickness direction of the sample part based on a fluorescent image for adjusting a focal position of the biological sample SPL obtained by the image obtaining unit 32.

The data recording unit 34 generates one image of the biological sample by coupling images of the biological sample of the sample part generated by the image obtaining unit 32, encodes the one image into sample data in a predetermined compression format such as JPEG (Joint Photographic Experts Group), and stores the encoded data in the data storage 35. This process may be performed before the distribution information calculation unit 33 calculates the distribution information.

Moreover, the data recording unit 34 receives the distribution information calculated by the distribution information calculation unit 33, and stores, in the data storage 35, the data in relation to the sample data.

The data storage 35 may store information such as data (e.g., area, number, and type of the fluorescent marker) of the result of measuring the fluorescent marker 55 by the distribution information calculation unit 33, the collector's name of the biological sample SPL, the gender and age of the collector, and the date of collection, for example.

Hereinabove, the functional block diagram for the process of obtaining the image of the biological sample has been described.

[Regarding Movement of Stage 11]

Now, the two types of movement of the stage 11 will be summarized. In one type of movement of the stage 11, the stage 11 is moved in order in the x-axis direction or the y-axis direction in order to sequentially perform the preliminary photographing on each section of the biological sample SPL in an x-y plane. This movement is the one shown in FIG. 5.

Then, the other type of movement of the stage 11 is performed every time the one type of movement is performed and a new section of the biological sample SPL is placed in the photographing range. The other type of movement of the stage 11 is integrative movement of the stage 11 in the x-axis direction, the y-axis direction, and the z-axis direction performed while exposing the image sensor 14 in order to take a fluorescent image for adjusting a focal position. Hereinafter, a method of taking a fluorescent image for adjusting a focal position with the other type of movement of the stage 11 will be described.

[Regarding Method of Taking Fluorescent Image for Adjusting Focal Position]

In the photographing of a fluorescent image for adjusting a focal point performed for each one type of movement of the stage 11, movement of the stage 11 by the stage control unit 31 and exposure of the image sensor 14 by the image obtaining unit 32 are performed in synchronization.

The stage control unit 31 moves the focal point of the optical system with respect to the sample part by moving the stage 11 in the x-y plane direction and the z-axis direction. In this embodiment, because the movement of the stage 11 is controlled, the focal point is moved in the thickness direction of the sample part (z-axis direction (optical axis direction of the objective lens 12A)), and in a plane direction perpendicular to the thickness direction (x-y plane direction).

As a specific example, the stage control unit 31 moves the position of the stage 11 according to the following formula.

[Mathematical Formula 1]

$$x(t) = x_0 + R \times \cos\left(2\pi \frac{t}{t_{ex}}\right) \quad (1)$$

$$y(t) = y_0 + R \times \sin\left(2\pi \frac{t}{t_{ex}}\right) \quad (2)$$

$$z(t) = z_{start} + (z_{end} - z_{start})\frac{t}{t_{ex}} \quad (3)$$

As shown in the following formulae (1) and (2), the stage 11 is moved along a circle having the central coordinate ($x_0$, $y_0$) and a radius of R on the x-y plane at a constant speed. The position of the central coordinate ($x_0$, $y_0$) and the size of the radius R may be arbitrarily set if an image in the photographing range AR can be taken.

However, if the size of the radius R is too small, it is difficult to separate a bright spot image at focused focal point to be described later from a defocused bright spot image in an image. Therefore, the radius R needs to be sufficiently larger than the size of the bright spot at the time of focusing. Specifically, because the size of a green focal image is about 0.3 μm in the case where NA is 0.8, the radius R desirably has a value sufficiently larger than the size of the bright spot image, e.g., a value larger than 2 to 3 μm.

In the formulae (1) and (2), $t_{ex}$ represents an exposure time period. Specifically, the stage 11 is circularly moved while the image sensor 14 is exposed. In other words, in this embodiment, the image sensor 14 is exposed while the stage 11 is circularly moved.

As shown in the formula (3), the stage 11 is moved also along the z-axis direction. The stage 11 is moved at a constant speed from $z_{start}$ being a movement start position to $z_{end}$ being a movement end position during the exposure time period of the image sensor 14.

Then, the image obtaining unit 32 sends a command of exposing the image sensor 14 to the photographing control unit 17 during the period from when movement of the stage 11 is started in order to take a fluorescent image for adjusting a focal position to when the movement of the stage 11 is finished.

Figure 6A:
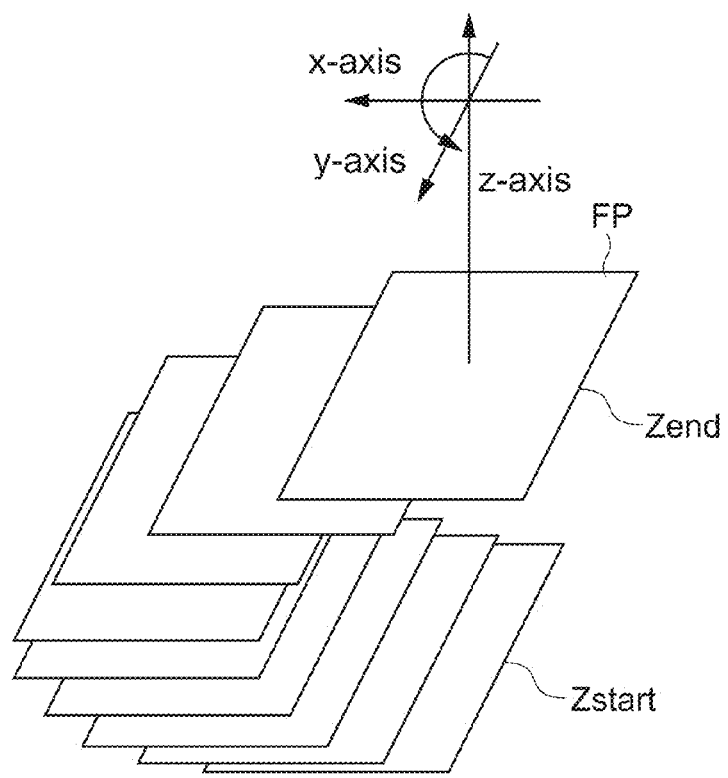
FIG. 6A is a schematic diagram showing movement of a focal position of an optical system in the case where the stage 11 is moved.
Figure 6B:
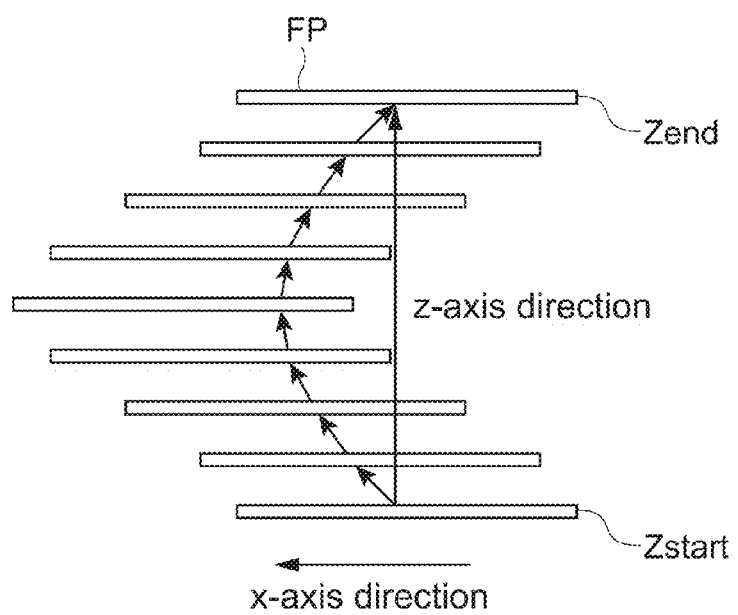
FIG. 6B is a schematic diagram showing the movement of the focal position of the optical system in the case where the stage 11 is moved.

FIGS. 6A and 6B are each a schematic diagram showing movement of a focal position of an optical system in the case where the stage 11 is moved. As shown in FIG. 6, a focal surface FP including a focal position is moved along the z-axis direction from $z_{start}$ to $z_{end}$. Moreover, the focal surface FP is moved circularly around the central coordinate ($x_0$, $y_0$) on the x-y plane.

The movement method of the stage 11 will be described in detail.

Figure 7:
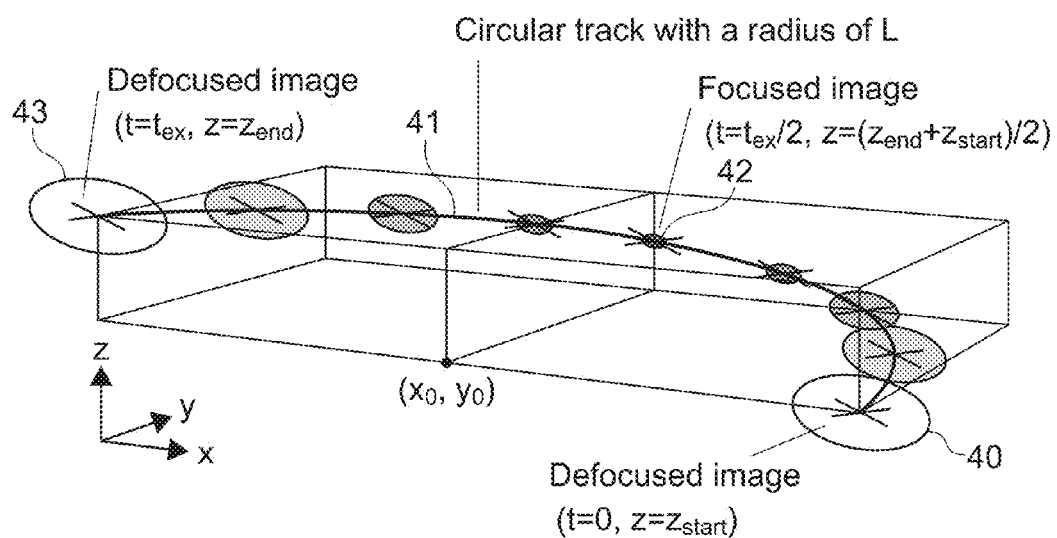
FIG. 7 is a diagram showing changes with time of a shape and a position of an image taken by an image sensor 14 due to the focal position changed by movement of the stage 11 at the time of exposure.

FIG. 7 is a diagram showing changes with time of a shape and a position of an image taken by an image sensor 14 due to the focal position changed by movement of the stage 11 at the time of exposure. The change in position of the image is represented by a locus 41.

As shown in FIG. 7, the stage control unit 31 moves the stage 11 in the z-axis direction from bottom to top at a constant speed, and moves the stage 11 circularly on the x-y plane at the constant speed. During the period from when the exposure is started to when the exposure is finished, a state where the objective lens 12A is not focused on the fluorescent marker 55 bonded to a specific gene changes to a focused state, and changes to a non-focused state again.

Specifically, at the exposure start position, a defocused image 40 of color-producing light having a circular shape, which is emitted from a fluorescent marker, is taken on the image sensor 14.

Then, it gradually comes into focus as the exposure time period elapses, and if the z-axis coordinate of an image at the exposure start position is represented by $z_{start}$, the z-axis coordinate of an image at the exposure end position is represented by $z_{end}$, and the exposure time period is represented by $t_{ex}$, a focused image 42 is taken on the image sensor 14 when the z-axis coordinate of the image is $(z_{end}+z_{start})/2$ and the exposure time period is $t_{ex}/2$. In the focused state, an image of color-producing light having a circular shape, which is emitted from a fluorescent marker, is small, the edge is clarified, and the brightness is high.

If the exposure time period elapses furthermore, the image becomes a defocused image again, and a defocused image 43 of color-producing light having a circular shape, which is emitted from a fluorescent marker, is taken on the image sensor 14, at the exposure end position.

As described above, on the image sensor 14, the images 40 to 43 are sequentially exposed, and an image having a semicircular shape is taken.

Hereinabove, the method of taking a fluorescent image for adjusting a focal position has been described.

[Regarding Repetition of Taking Fluorescent Image for Adjusting Focal Position in Z-Axis Direction]

When taking a fluorescent image for adjusting a focal position, as described above, the focal position in the z-axis direction is moved from $z_{start}$ to $z_{end}$ being the movement end position. However, all of the photographing range in the z-axis direction are not necessarily covered by the movement in the z-axis direction at one time. Therefore, the photographing range in the z-axis direction is divided into a plurality of ranges, and a fluorescent image for adjusting a focal position is taken a plurality of times.

Figure 8A:
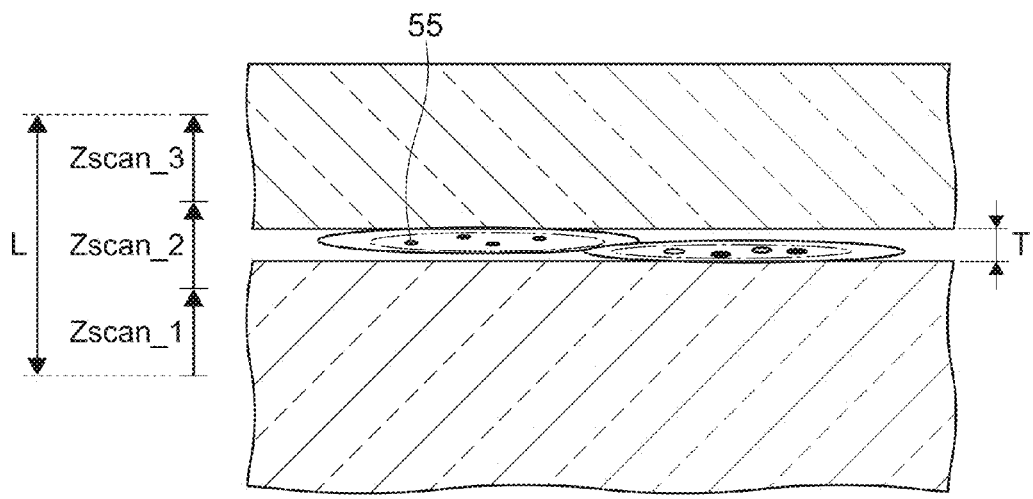
FIG. 8A is a schematic diagram for explaining a range of movement of the focal position according to this embodiment in detail.
Figure 8B:
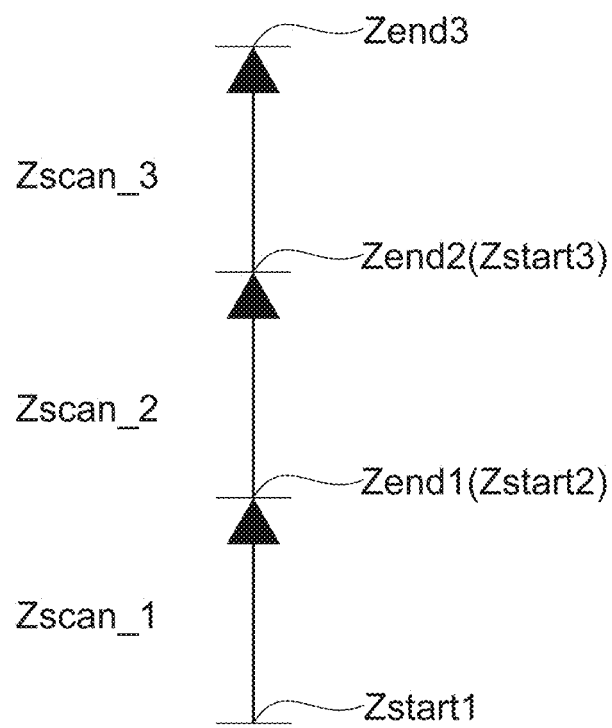
FIG. 8B is a schematic diagram for explaining the range of movement of the focal position according to this embodiment in detail.

FIGS. 8A and 8B are each a schematic diagram for explaining a range of movement of the focal position according to this embodiment in detail. As shown in FIG. 8, in this embodiment, a plurality of divided photographing ranges (Zscan_1 to 3), which are obtained by dividing, in the z-axis direction, a photographing range L including at least a range T of the thickness of the sample part, are set. In each of the divided photographing ranges, a fluorescent image for adjusting a focal position is taken. Specifically, in each divided photographing range, $z_{start}$ (1 to 3) and $z_{end}$ (1 to 3) are set (see FIG. 8B).

The size of the divided photographing ranges in the z-axis direction is, for example, 20 μm to 50 μm. However, the size is not limited to the value. Moreover, the number of divided photographing ranges is also not limited. Moreover, the size of the photographing range L including at least the range T of the thickness of the sample part is also not limited.

In a state where a predetermined sample part is allocated in the photographing range AR, the focal position is moved in each of the plurality of divided photographing ranges. Then, a fluorescent image for adjusting a focal position is obtained for each divided photographing range. In this embodiment, because the photographing range is divided into three ranges in the z-axis direction, three fluorescent images for adjusting a focal position are obtained with respect to a predetermined sample part.

For example, three fluorescent images may be sequentially taken in a state where a predetermined sample part is allocated. Alternatively, after an image of the entire biological sample SPL is taken by using one divided photographing range, an image in another divided photographing range may be taken.

[Specific Example of Fluorescent Image for Adjusting Focal Position]

Figure 9:
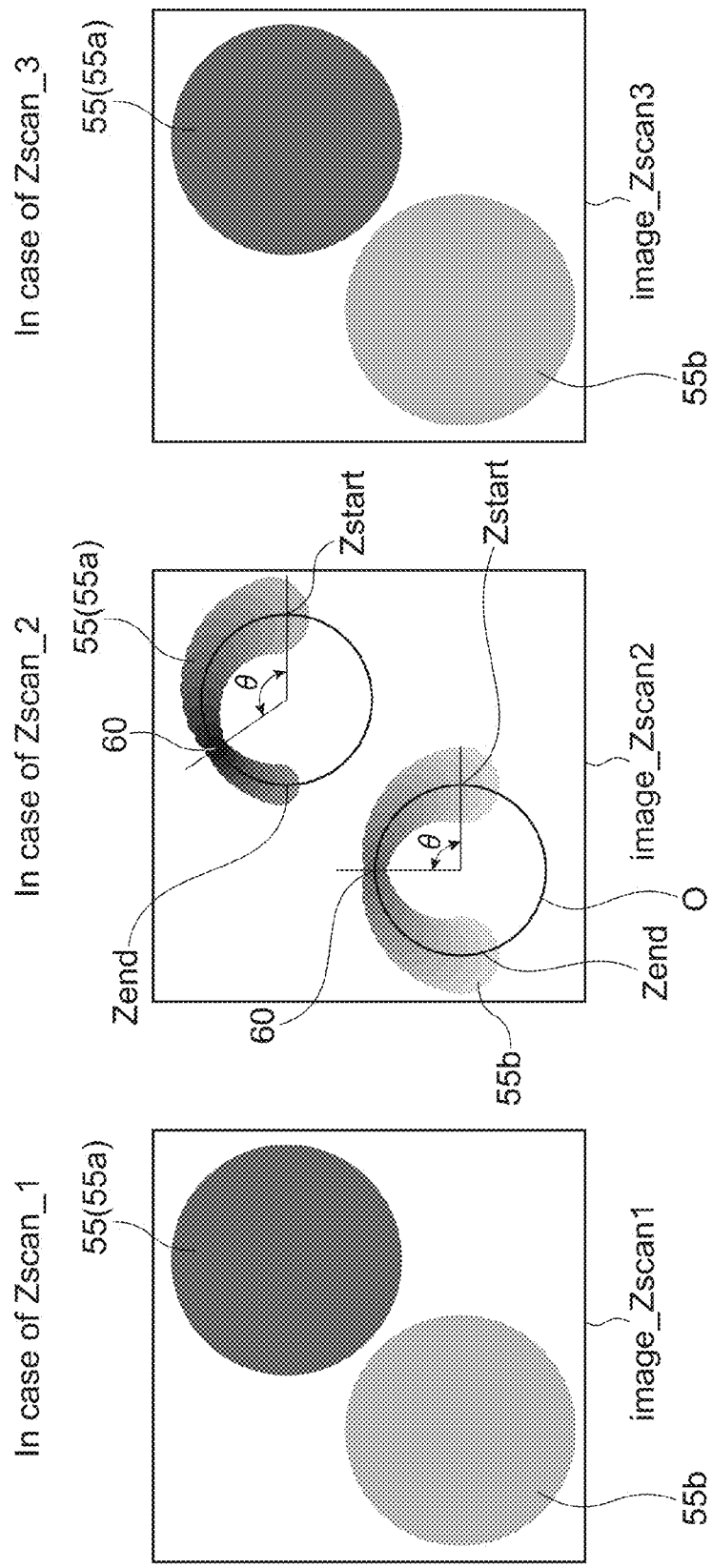
FIG. 9 is a schematic diagram showing a fluorescent image of a sample part taken in each divided photographing range.
Figure 10:
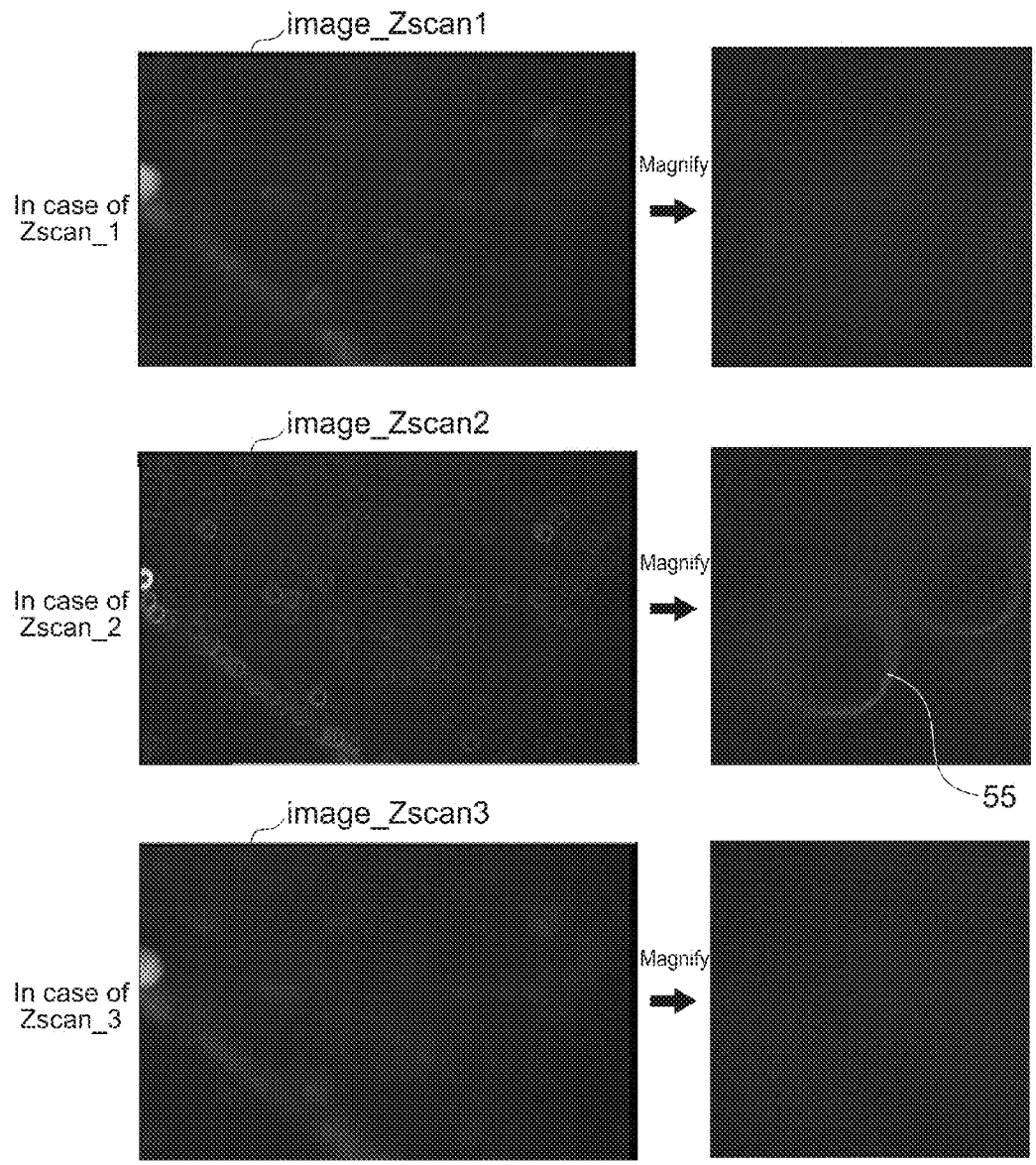
FIG. 10 shows photographs taken as an example of this embodiment, which correspond to the respective fluorescent images shown in FIG. 9.

FIG. 9 is a schematic diagram showing a fluorescent image of a sample part taken in each of the plurality of divided photographing ranges (Zscan_1 to 3). Moreover, FIG. 10 shows photographs taken as an example of this embodiment, which correspond to the respective fluorescent images shown in FIG. 9. These photographs are fluorescent images taken under conditions in which the radius R of circular orbital is 15 μm, the movement amount in the z-axis direction ($z_{end}-z_{start}$) is 20 μm, and the exposure time period of the image sensor 14 is 1 sec as photographing conditions. In addition thereto, a photographing condition such as a gamma value is adjusted as appropriate.

The divided photographing ranges Zscan_1 and 3 are photographing ranges not including the fluorescent marker 55 in the z-axis direction. Therefore, in image_Zscan1 and 3 being fluorescent images taken in the ranges, the image of the fluorescent marker 55 is very defocused (in the cases of the Zscan_1 and Zscan_3 in respective figures).

On the other hand, in image_Zscan2 being a fluorescent image taken in the divided photographing range Zscan_2, the focal position is moved in a range including a position at which the fluorescent marker 55 exists. Therefore, in the taken image_Zscan2, an image of a locus in which the fluorescent marker 55 is focused on along with the movement of the focal position is taken, as shown in the case of the Zscan_2 in respective figures.

[Regarding Process of Calculating Distribution Information of Fluorescent Marker 55]

Next, a process of calculating the distribution information of the fluorescent marker 55 will be described.

Based on a plurality of fluorescent images taken in each of the plurality of divided photographing ranges (Zscan_1 to 3), distribution information of the fluorescent marker 55 in the thickness direction of the sample part is calculated. As described above, the calculation is performed by the distribution information calculation unit 33.

Figure 11:
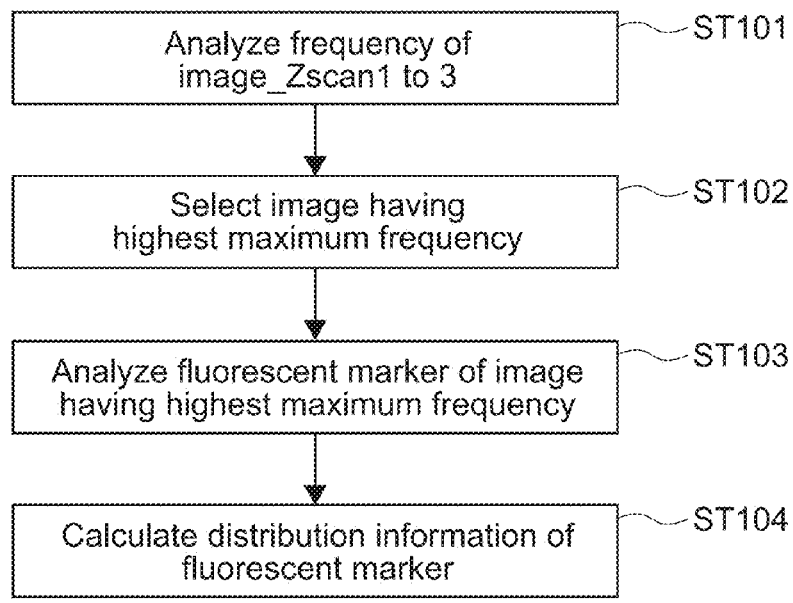
FIG. 11 is a flowchart showing an example of a calculation process performed by a distribution information calculation unit.

FIG. 11 is a flowchart showing an example of a calculation process performed by the distribution information calculation unit 33.

First, the distribution information calculation unit 33 performs frequency analysis of a plurality of fluorescent images taken in each of the divided photographing ranges Zscan_1 to 3 (step 101)

Accordingly, the spatial frequency of each of the plurality of fluorescent images (image_Zscan1 to 3) is calculated.

Next, the distribution information calculation unit 33 compares the maximum frequency component of the fluorescent images with each other, and selects a fluorescent image having the highest maximum frequency component (step 102).

In the fluorescent images image_Zscan1 and 3, the image of the fluorescent marker 55 is defocused. On the other hand, in the fluorescent image image_Zscan2, a focused image of a locus of the fluorescent marker 55 is shown. Therefore, in step 102, the fluorescent image image_Zscan2 is selected as a fluorescent image having the highest maximum frequency component.

Next, the distribution information calculation unit 33 analyzes the image of the locus of the fluorescent marker 55 in the fluorescent image image_Zscan2 having the highest maximum frequency component (step 103).

Specifically, in this embodiment, the number and shape of the fluorescent marker 55 in the fluorescent image image_Zscan2 are analyzed in this step. Hereinafter, this analysis is referred to as shape analysis of a fluorescent marker. By the shape analysis, an angle θ between an exposure start position $z_{start}$ of the shape of the fluorescent marker and a focused image 60 is obtained. The description thereof will be made later in detail.

Last, the distribution information calculation unit 33 calculates distribution information of each of the plurality of fluorescent markers 55 in the thickness direction of the sample part based on the angle θ between the exposure start position $z_{start}$ and the focused image 60, calculated for each fluorescent marker 55 (step 104).

Specifically, in this embodiment, positional information in the z-axis direction is calculated for each fluorescent marker 55. Therefore, distribution information of the plurality of fluorescent marker 55 can be calculated.

Hereinabove, the method of calculating distribution information of the fluorescent marker 55 has been described.

[Regarding Shape Analysis of Fluorescent Marker and Marker Color]

Now, a marker color in the shape analysis of a fluorescent marker performed when the distribution information of the fluorescent marker 55 is calculated will be described.

The distribution information calculation unit 33 detects the fluorescent marker 55 (hereinafter, referred to also as "target marker" and described as a fluorescent marker 55a) that labels the target biological tissue 50 from the fluorescent image image_Zscan2 obtained by the image obtaining unit 32.

On the distribution information calculation unit 33, a color displayed by the target marker (hereinafter, referred to as "target marker color") and a color displayed by the fluorescent marker 55 (hereinafter, referred to as "nucleus marker") that labels cell nuclei (hereinafter, referred to as nucleus marker color) are set as setting information, for example.

Moreover, in the case where the fluorescent marker 55 that labels a gene to be selected as controls (hereinafter, referred to as "control marker" and described as a fluorescent marker 55b) is used, the number of genes selected as controls existed in a normal cell nucleus is also set on the distribution information calculation unit 33. Moreover, in this case, a color displayed by a fluorescent marker that labels the control gene (hereinafter, referred to as "control marker color") is also set.

The setting information is unambiguously determined depending on the manufacturer of a probe to be used for fluorescence stain and usage conditions such as a type of a fluorescent marker. Specifically, in the case of the HER-2DNA probe kit manufactured by ABBOTT JAPAN CO., LTD, for example, the target marker color of the HER2 gene is set to be "red," and the nucleus marker color is set to be "blue." Moreover, in this case, a gene positioned adjacent to the HER2 gene on a chromosome is the control gene, and the control marker color of the control gene is set to be "green."

The distribution information calculation unit 33 detects the shape (area) and number of the fluorescent markers 55 by displaying each set marker color and detecting brightness higher than that of a threshold value. Then, the shape of the fluorescent marker 55 is analyzed, and thus the distribution information of the plurality of fluorescent markers 55 is calculated.

[Regarding Analysis of Shape of Fluorescent Marker (Specific Example)]

Now, a specific example of analysis of the shape of a fluorescent marker performed when the distribution information of the fluorescent marker 55 is calculated will be described.

In the case of the Zscan_2 shown in FIG. 9, a locus obtained by taking an image of the two fluorescent markers 55a and 55b by the above-mentioned method is illustrated as an example. As described above, the fluorescent image image_Zscan2 is taken by exposing the image sensor 14 while the focal position of the optical system 12 is moved.

Because the focal position is moved circularly in the x-y plane being a plane direction of the stage 11, the fluorescent markers 55a and 55b are moved along a circle O. Specifically, the locus of the fluorescent markers 55a and 55b are moved in a semicircular motion from $z_{start}$ being a movement start position of a focal point to $z_{end}$ being a movement end position (here, the case where the focal position is moved on the semicircle during the exposure time period is illustrated).

The focal position of the optical system 12 is moved upward in the z-axis direction in the divided photographing range Zscan_2. At any one of focal positions during the movement, it most comes into focus on one of the fluorescent marker 55a and the fluorescent marker 55b. In the most-focused state, the areas of the images of the fluorescent marker 55a and 55b are smallest and the brightness is highest. The image with the smallest area is referred to as focused image 60.

In this embodiment, the distribution information calculation unit 33 calculates the angle θ between the start position $z_{start}$ and the focused image 60, and calculates the distribution information of the fluorescent marker 55 in the thickness direction of the sample part based on the angle θ. An example of the method of calculating the angle θ will be described later.

For example, in the case of fluorescent marker 55b shown in the case of the Zscan_2 in FIG. 9, the angle θ is about 90 degrees because the focused image 60 exists at the center position of the locus of the fluorescent marker 55b, which is moved in a semicircular motion. In this case, it most comes into focus when the focal position is moved on the center of the divided photographing range Zscan_2. Therefore, it can be seen that the fluorescent marker 55b is positioned at the center of the divided photographing range Zscan_2.

In the case of the other fluorescent marker 55a, the focused image 60 exists at a position closer to the end position $z_{end}$ than the center position of the locus of the fluorescent marker 55a, which is moved in a semicircular motion. The angle θ is about 135 degrees. In this case, it most comes into focus when the focal position is moved beyond the center of the divided photographing range Zscan_2 and in an upper portion thereof. Therefore, it can be seen that the fluorescent marker 55a is positioned in an upper portion of the divided photographing range Zscan_2.

Specifically, as the angle θ between the exposure start position $z_{start}$ and the focused image 60 becomes smaller, the fluorescent marker 55 is located at a position closer to the start position $z_{start}$. Specifically, the fluorescent marker 55 is positioned at a side close to the stage 11 in the biological sample SPL.

On the other hand, as the angle θ between the exposure start position $z_{start}$ and the focused image 60 becomes larger, the fluorescent marker 55 is located at a position closer to the end position $z_{end}$. Specifically, the fluorescent marker 55 is positioned at a side away from the stage 11 in the biological sample SPL.

It should be noted that the description has been made on the assumption that the movement of the stage 11 in the z-axis direction and in the x-y plane is performed at a constant speed. However, the movement of the stage 11 in the z-axis direction and in the x-y plane is not necessarily performed at a constant speed. It should be noted that in this case, there is a need to set the movement amount of the stage 11 in the x-y plane, i.e., correlation information of the one-to-one relationship of the angle θ and the movement amount of the stage 11 in the z-axis direction in advance, and store the information.

Hereinabove, a specific example of analysis of the shape of the fluorescent marker has been described.

[Regarding Calculation of Angle θ Between Exposure Start Position $z_{start}$ and Focused Image 60]

Now, a specific example of a method of calculating the angle θ performed when the distribution information of the fluorescent marker 55 is calculated will be described.

Figure 12:
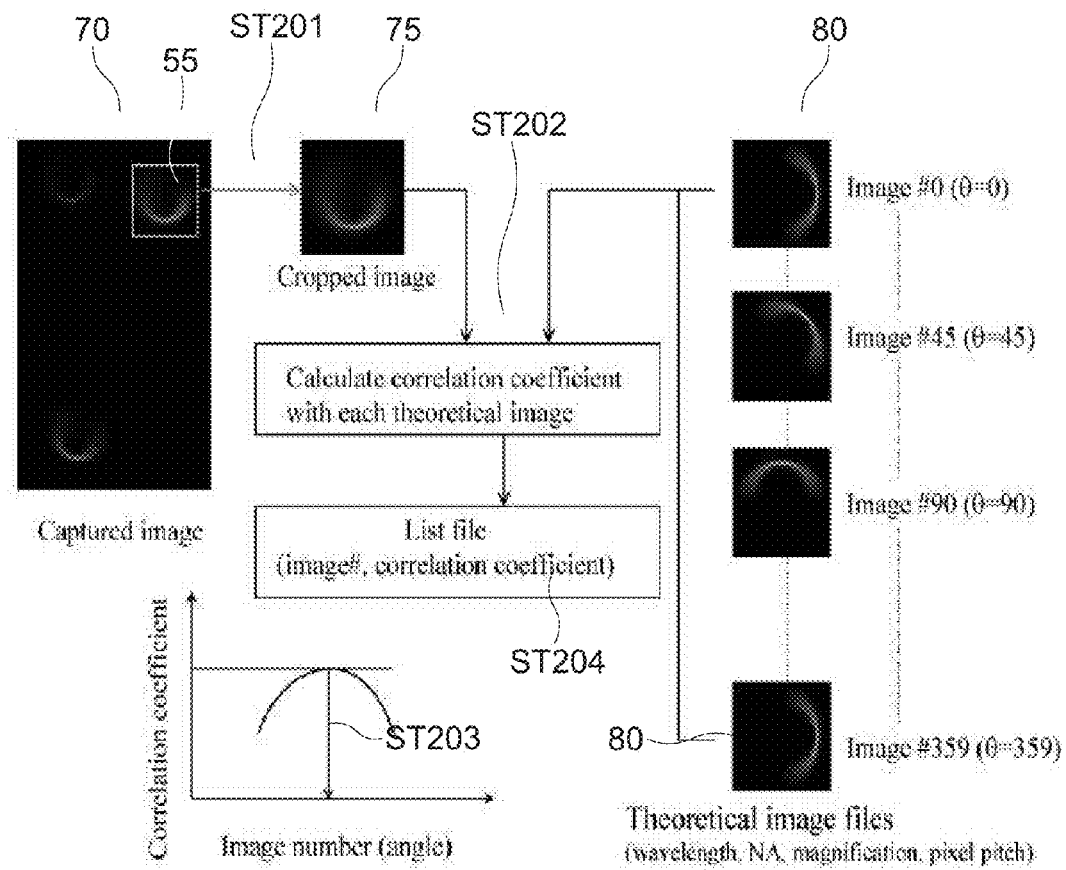
FIG. 12 is a diagram showing an example of a process of calculating an angle $\theta$ between a start position according to this embodiment and a focused image.

FIG. 12 is a diagram showing an example of a process of calculating the angle θ between the exposure start position $z_{start}$ according to this embodiment and the focused image 60.

First, the distribution information calculation unit 33 cuts, by a trimming process, an image of the fluorescent marker 55 to be analyzed from a fluorescent image 70 for adjusting a focal position (step 201).

A matching process is performed on a cut trimming image 75 with a theoretical image. As shown in FIG. 12, in this embodiment, a file of theoretical images is stored in the storage 27 or the like in advance. In the file, a plurality of theoretical images 80 linked with respective angles of 0 to 359 degrees are stored. In this embodiment, the magnitude of the linked angle is an identification number of the theoretical image 80.

The wavelength, numerical aperture, magnification, pixel pitch, and the like for creating the theoretical image 80 in advance may be set as appropriate. Moreover, which angle is set as 0 degree, for every what degrees of angle the theoretical image is prepared, or the like may be also set as appropriate. For example, in the case where the theoretical image 80 is prepared for every 1 degree, 360 theoretical images 80 are created.

Next, the distribution information calculation unit 33 calculates the correlation coefficient between the plurality of theoretical images 80 and the trimming image 75 (step 202).

Then, the distribution information calculation unit 33 calculates the identification number of the theoretical image 80 having the highest correlation coefficient (step 203, see graph of FIG. 11).

Last, the distribution information calculation unit 33 calculates the identification number of the theoretical image 80 having the highest correlation coefficient with respect to the plurality of fluorescent markers 55 of the captured image 70, generates a list of the identification numbers associated with the plurality of fluorescent marker 55, and causes the storage 27 or the like to store the list (step 204).

In the above-mentioned method, the angle θ between the above-mentioned start position $z_{start}$ and the focused image 60 is appropriately calculated based on the identification number (angle) of the theoretical image 80 calculated depending on the respective fluorescent markers 55. For example, the theoretical image 80 may be prepared so that the angle θ corresponds to the angle being the identification number. Alternatively, the shape of the fluorescent marker 55 is determined by the angle being the identification number, and then the angle θ between the start position $z_{start}$ and the focused image 60 may be calculated again. It should be noted that the method of calculating the angle θ between the start position $z_{start}$ and the focused image 60 is not limited to the above-mentioned method, and another method may be used.

Hereinabove, the method of calculating the angle θ has been described.

[Regarding Specific Example and Method of Using Distribution Information of Fluorescent Marker]

Now, a specific example and method of using distribution information of a fluorescent marker will be described.

Figure 13:
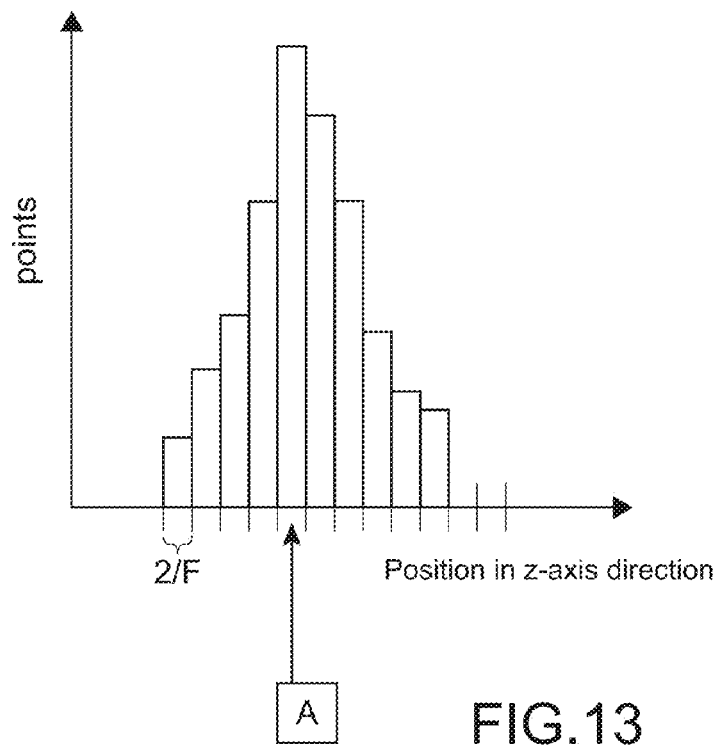
FIG. 13 is a graph showing an example of distribution information of a plurality of fluorescent markers according to this embodiment.
Figure 14:
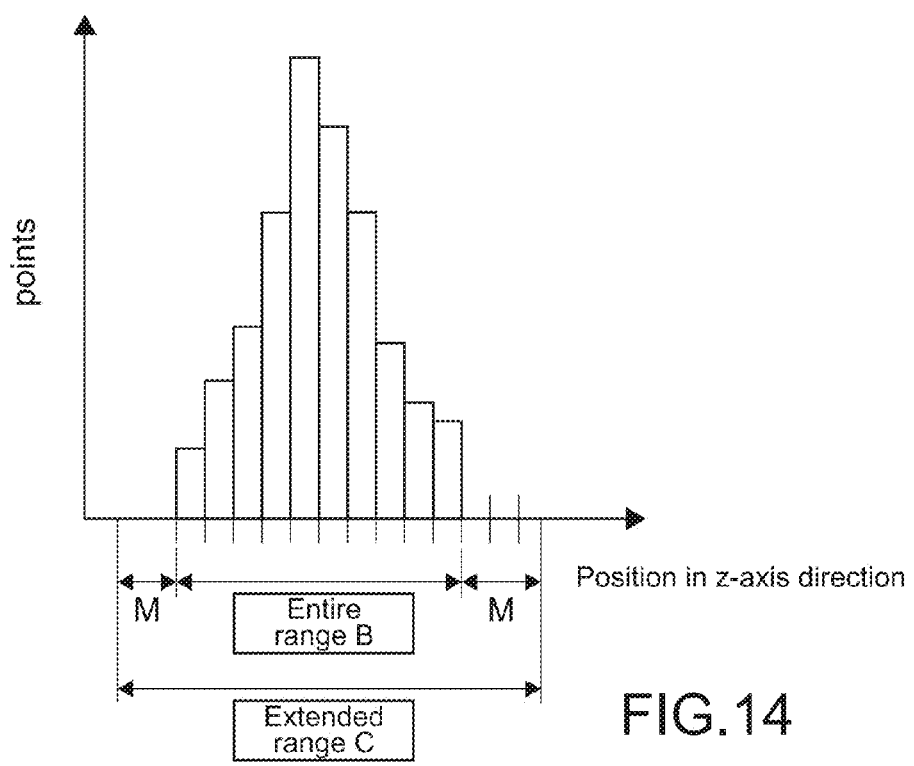
FIG. 14 is a graph showing an example of the distribution information of the plurality of fluorescent markers according to this embodiment.
Figure 15:
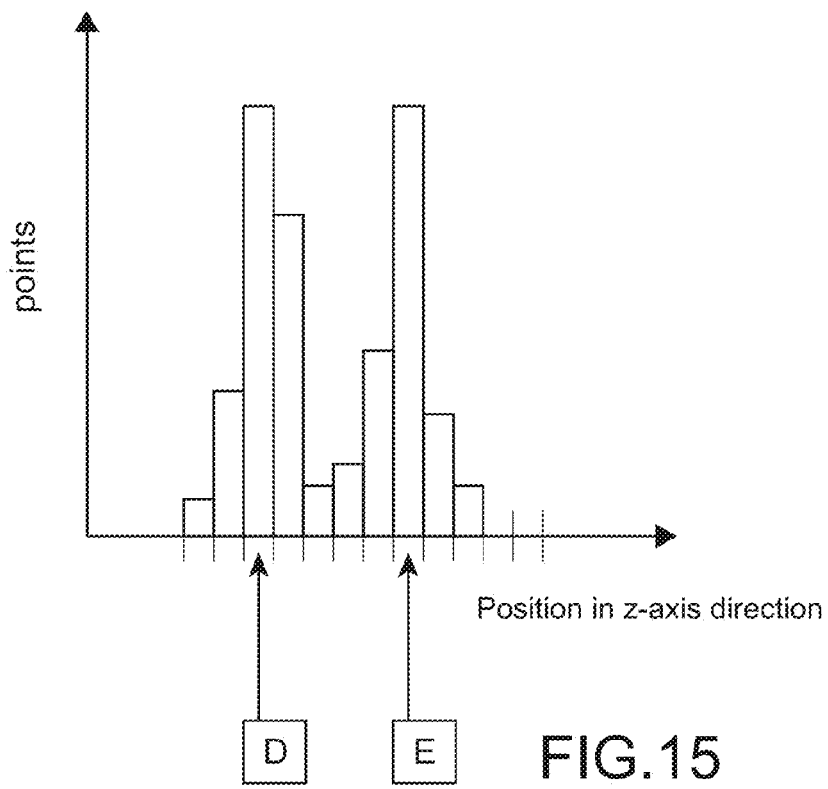
FIG. 15 is a graph showing an example of the distribution information of the plurality of fluorescent markers according to this embodiment.

FIGS. 13 to 15 are each a graph showing an example of distribution information of the plurality of fluorescent markers 55. As described above, the distribution information of the fluorescent marker 55 can be generated as data in the format of a histogram. In these graphs, the horizontal axis represents a position of the fluorescent marker 55 in the z-axis direction, and the vertical axis represents the number of the fluorescent markers 55.

In this embodiment, the horizontal axis is separated by the half size of the focal depth F of the objective lens (F/2), and the number of the fluorescent markers 55 included in each range is counted. The resolution of the horizontal axis is not limited to F/2, and a value smaller than the focal depth may be set as appropriate. Moreover, a value larger than the focal depth may be set.

Specifically, if the focal position of the optical system 12 is set within a range of the horizontal axis, the focused image of the fluorescent marker 55 included in the range is taken. A more defocused image of the fluorescent marker 55 included in another range is taken as it is away from the focal position.

Based on such distribution information of the fluorescent marker 55, an image of the biological sample SPL is taken. Because it is possible to refer to the distribution of the fluorescent marker 55, the actual photographing can be performed efficiently and accurately depending on the photographing mode and photographing purpose.

For example, it is assumed to be a purpose to take a fluorescent image in the actual photographing such that a certain number of fluorescent markers 55 out of the plurality of fluorescent markers 55 existed in the biological sample SPL only have to be focused on. In this case, as shown in FIG. 13, it is determined that the actual photographing in which a position A included in a range having highest number of the fluorescent markers 55 is focused on only has to be performed. Accordingly, it is possible to take a fluorescent image in the actual photographing accurately.

Moreover, for example, it is assumed to be a purpose to quantitatively observe the number or type of the whole fluorescent markers 55 included in the biological sample SPL, or the like. In this case, as shown in FIG. 14, by calculating an entire range B in which the fluorescent markers 55 are positioned from the distribution information, and scanning the entire range B, it is possible to take a fluorescent image including all of the fluorescent markers 55.

Moreover, one fluorescent image may be taken by exposing the image sensor 14 while moving the focal position from the start position to the end position of the entire range B. Moreover, the focal position may be moved in an extended range C obtained by adding a predetermined margin M to both sides of the entire range B. Accordingly, almost similarly defocused images of the fluorescent marker 55 positioned at the center of the entire range B and of the fluorescent marker 55 positioned at the end are taken. Specifically, because images of the whole fluorescent markers 55, which have almost similar sizes and brightness, are taken, it is possible to improve the measurement accuracy of the fluorescent marker 55.

There is a photographing mode referred to as so-called Z-stack, in which a plurality of fluorescent images are taken at different focal positions in the z-axis direction with respect to one sample part. Also in the case where the Z-stack is performed, the distribution information can be used as appropriate. For example, by referring to the entire range B shown in FIG. 14, the range for performing the Z-stack is determined. Moreover, by referring to the graph, the interval between different focal positions, the number of photographing, and the like may be set as appropriate. For example, the Z-stack may be performed depending on the range separating the horizontal axis. As described above, by referring to the distribution information, it is possible to take a fluorescent image with high accuracy.

Moreover, as shown in FIG. 15, the case where the graph of the distribution of the fluorescent marker 55 is separated into two mountain parts is conceivable. Specific examples of such a case include the case where the distribution of the fluorescent marker 55 is centered near two different positions. In this case, because a certain number of fluorescent markers 55 only have to be focused on, if the photographing is performed at the center position, the photographing may be failed.

By referring to the distribution information, a position D and a position E included in the mountain parts are calculated as the focal position. By focusing on the positions and performing the photographing two times, it is possible to successfully take a fluorescent image with high accuracy in the actual photographing.

Hereinabove, a specific example and method of using distribution information of a fluorescent marker has been described.

[Overview of Present Disclosure]

Hereinabove, in the image obtaining apparatus 100 according to this embodiment, the focal position of the optical system 12 is moved in the photographing range L including at least the range T of the thickness of the sample part. The image sensor 14 is exposed during the movement, and a fluorescent image of the biological sample SPL is obtained. Then, based on the fluorescent image of the biological sample SPL, the distribution information of the fluorescent marker 55 in the thickness direction of the sample part (z-axis direction) is calculated. Accordingly, it is possible to easily calculate a focal position for taking an image of the fluorescent marker 55 appropriately depending on the photographing mode and photographing purpose, for example. As a result, it is possible to efficiently take an image of the biological sample SPL to which the fluorescent marker 55 is attached.

[Problem in Existing Techniques (Problem of Number of Photographing)]

For example, a method of searching for a focal position by taking an image every time the focal position is changed at an interval smaller than the focal depth, and analyzing each taken image is assumed. The method needs to take a lot of images, and needs a high-capacity memory for storing data in the amount of the taken images. Moreover, because the method needs to refer to data of a plurality of images in order to calculate a focal position, it takes a lot of man-hours and is inefficient.

Specifically, in the case where NA is 0.8, the focal depth is about 1 μm. Then, the assumption is made that a focal position is searched for by taking a plurality of images while changing the focal position by, for example, 1 μm, to search for the focal position, and analyzing the image. In this case, there is a need to take 50 or more images and store them if the measurement is performed while changing the focal position by 1 μm in the range more than 50 μm. In the case where an imager of 24 M pixels at 14 bits is used, one image file has capacity of about 100 MB in tif format. Therefore, because a memory of 5 GB or more is necessary to process 50 or more images, the process is complicated.

[Advantage Obtained by Present Disclosure (Reducing of Number of Photographing)]

In this embodiment, as shown in FIG. 8, the Zscan_1 to 3 are set as three divided photographing ranges. As described above, a range larger than the focal depth is set, and distribution information is calculated by the small number of times of photographing. Accordingly, it is possible to search for a focal position with the significantly reduced number of photographing.

[Reason for Setting Photographing Range L to Large]

Figure 16:
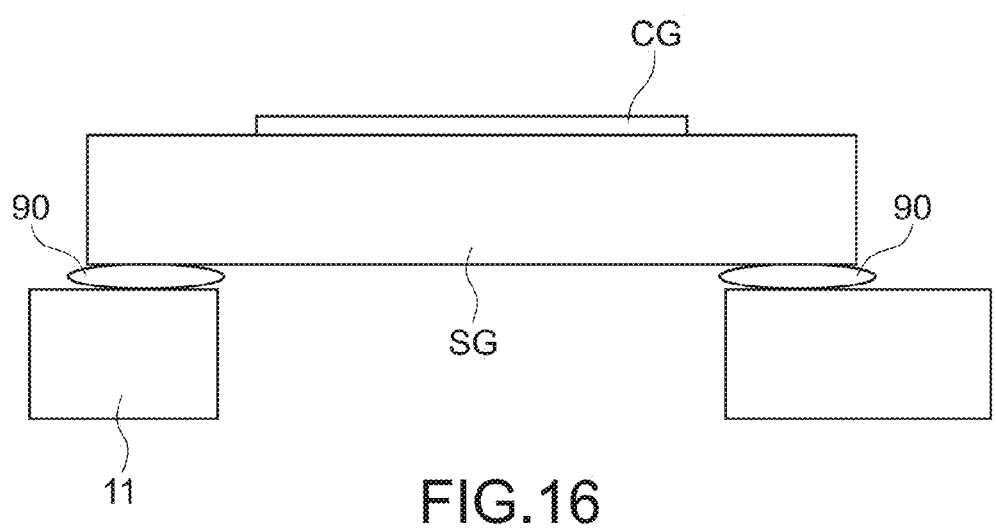
FIG. 16 is a schematic diagram showing a state where dust or the like is sandwiched between a glass slide and a stage.

In FIG. 8A, the photographing range L including the range in which the biological sample SPL are not located is set (Zscan_1 and 3). For example, as shown in FIG. 16, a dust 90 (having a size of about 20 μm to 50 μm, for example) such as hair is sandwiched between the glass slide SG and the stage 11 in some cases. In such a case, if the photographing range L is set taking into account of only the thickness of the glass slide SG, for example, it is highly likely to miss the focal position. Therefore, by setting the photographing range L including the range in which the biological sample SPL does not exist as appropriate, it is possible to calculate the distribution information of the fluorescent marker 55 accurately. As described above, because it is possible to search for a focal position by the small number of photographing, the photographing range L can be set large.

[Advantage Obtained in Present Disclosure (Removing of Effect Due to Dust Etc.)]

In the case where the focal position is automatically searched for and adjusted, an error in which a dust on the imager or defect of the imager is erroneously recognized as a fluorescent bright spot on the glass slide GS, and a position different from the true focal position is determined as the focal position, may be occurred.

In this embodiment, in steps 101 and 102 shown in FIG. 11, the respective spatial frequencies of the fluorescent images image_Zscan1 to 3 are calculated, and the image having the highest maximum frequency is selected. As described above, by analyzing the frequency components and comparing them, it is possible to select the fluorescent image image_Zscan2 including the focused image 60 of the fluorescent marker 55 without being affected by the dust on the imager (image sensor 14), defect of the imager, or the like.

Modified Example 1

Selection of Fluorescent Image by Brightness

Embodiments according the present disclosure are not limited to the above-mentioned embodiments and various modifications can be made.

Figure 17:
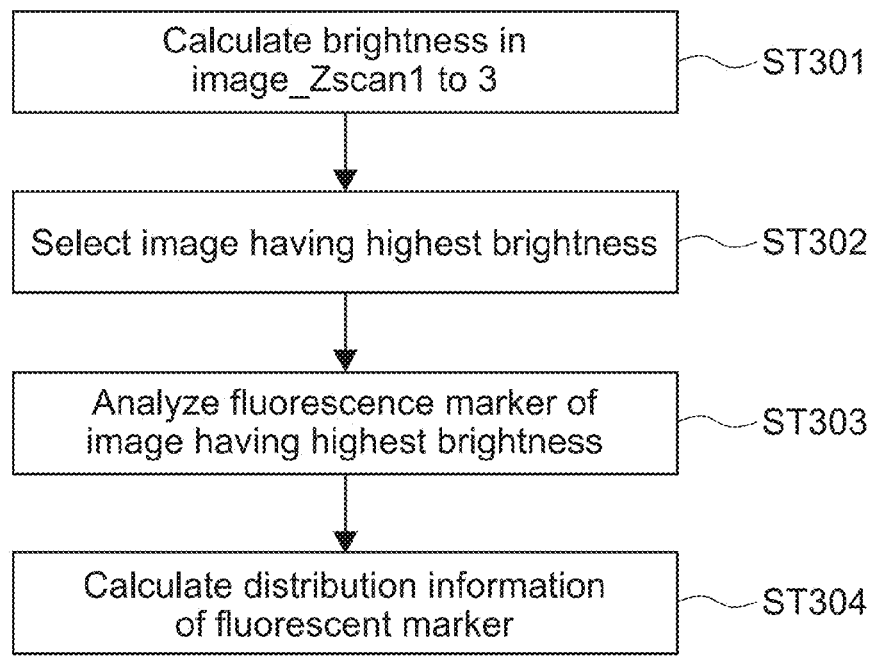
FIG. 17 is a flowchart showing a modified example of the calculation process performed by the distribution information calculation unit.

FIG. 17 is a flowchart showing a modified example of the calculation process of distribution information of the fluorescent marker 55 performed by the distribution information calculation unit 33 shown in FIG. 11.

In this modified example, first, the brightness in each of the fluorescent images image_Zscan1 to 3 is calculated (step 301).

Then, a fluorescent image having the highest brightness is selected (step 302).

Then, a process of analyzing a fluorescent marker is performed on the selected fluorescence image (step 303).

As described above, based on the brightness of each of the fluorescent images taken in the plurality of divided photographing ranges, a fluorescent image on which the calculation process of distribution information is performed may be selected. Accordingly, it is possible to reduce the calculation amount.

Modified Example 2

Integration of Photographing Range L

In the above-mentioned embodiment, as shown in FIG. 8A, a plurality of divided photographing ranges obtained by dividing the photographing range L are set, and a fluorescent image is taken for each of the divided photographing ranges. However, a fluorescent image may be generated by moving the stage so that the entire photographing range L is scanned in one photographing. Then, based on the fluorescent image, the distribution information of the fluorescent marker 55 may be calculated.

For example, one photographing may be performed in the photographing range L having a size of about 100 μm. Accordingly, it is possible to reduce the calculation amount, and to increase the processing speed, for example. Whether or not the divided photographing range is set may be determined based on the size of the photographing range L and the accuracy of the image sensor 14, for example.

Modified Example 3

Determination of Photographing Mode Based on Distribution

In the above, the description in which it is possible to use the distribution information as appropriate depending on the photographing mode and the photographing purpose has been made. Reversely, based on the distribution information, the optimal photographing mode and the photographing purpose may be selected.

For example, a determination process in which one photographing with a fixed focal position is selected in the case where the plurality of fluorescent markers 55 are centered in the range of focal depth, and the photographing by the Z-stack is selected in the case where the plurality of fluorescent markers 55 are dispersed may be performed. At this time, for example, the data processing unit 20 functions as the photographing mode determination unit.

Modified Example 4

Calculation of Distribution Information Based on Marker Color

Moreover, only a target marker (red) or control marker (green) out of the fluorescent markers 55 may be set as a target of the calculation of the distribution information. These settings may be input by a user's operation, for example.

Modified Example 5

Thinning Out of Fluorescent Marker to be Calculated

Moreover, positional information does not have to be calculated with respect to all of the fluorescent markers 55 in the fluorescent image. Specifically, the fluorescent markers 55 are thinning out and are selected, and distribution information may be calculated based on the positional information.

Modified Example

Others

It should be noted that in the configuration of the microscope 10 according to the above-mentioned embodiment, the objective lens 12A may be an ocular lens.

Moreover, although the stage 11 is moved to move the focal position in the above-mentioned embodiment, the objective lens 12A of the optical system 12 may be moved.

Although the data storage 35 is provided in the data processing unit 20, and the image of the biological sample, distribution information of the fluorescent marker 55, and the like are stored in the data storage 35 in the above-mentioned embodiment, they may be stored in external storage.

In order to connect the microscope 10 and the data processing unit 20, not only a bus transmission path but also a wired or wireless transmission medium such as a local area network, the Internet, and digital satellite broadcasting may be used.

Second Embodiment

In the second embodiment, a state where the cell density in the biological sample SPL photographed by a fluorescent microscope is high, and each of bright spots of a fluorescent image obtained by staining the cells by a fluorescent label is not distinguished clearly is mainly assumed.

Moreover, even if the bright spots can be distinguished, because the number of the bright spots is large, also a case where it takes too much time to perform analysis is assumed in the algorithm in which the shape of each locus of bright spots is analyzed, which is described in the first embodiment.

Therefore, a feature of the present disclosure in the second embodiment is to regard the whole image as texture without distinguishing each bright spot of a fluorescent image, and to analyze the texture. With the method, it is possible to reduce the processing time in the case where the cell density is high, as compared with the case of the algorithm in which the shape of each locus of bright spots is analyzed, which is described in the first embodiment.

It should be noted that in the following, the description will be made with the same member as that in the first embodiment denoted by the same number, unless otherwise noted.

[Regarding Specific Difference from First Embodiment]

First, a specific difference from the first embodiment will be described. The specific difference from the first embodiment is a part of a paragraph of [Regarding Calculation of Angle θ between Exposure Start Position $z_{start}$ and Focused Image 60] that describes the method of calculating the angle θ in the first embodiment. In the first embodiment, the trimming image 75 cut from the fluorescent image 70 for adjusting a focal position and the correlation coefficient with the plurality of theoretical images 80 linked with respective angles of 0 to 359 degrees are calculated for each trimming image 75.

On the other hand, in this embodiment, the entire fluorescent image for adjusting a focal position is analyzed as texture, and the angle θ is calculated by any of two types of methods to be described later. This is the major difference in this embodiment.

Examples of an associated difference along with the analysis of the entire fluorescent image include that in this embodiment, it may be impossible to obtain the distribution of the individual fluorescent marker 55, and an average position of all of the fluorescent markers 55 is obtained unlike the first embodiment.

[Regarding Entire Flow Including Actual Photographing]

Now, a flow of the entire process will be described in order to summarize the relationship between the preliminary photographing, the analysis according to the first embodiment, the analysis according to the second embodiment, and the actual photographing.

Figure 18:
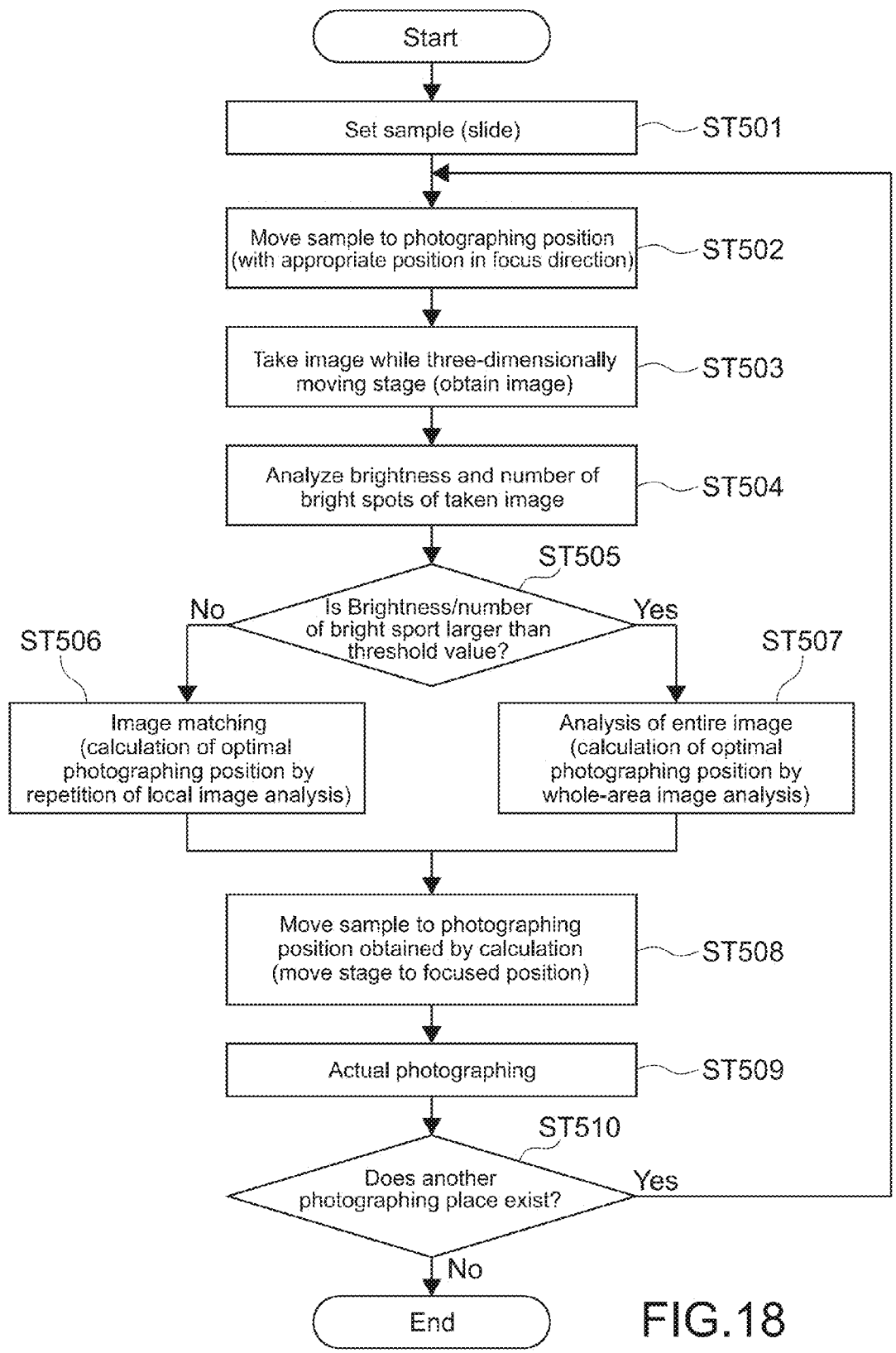
FIG. 18 is a flowchart showing a flow of the entire process including a relationship between preliminary photographing, analysis according to a first embodiment, analysis according to a second embodiment, and actual photographing, in the present disclosure.

FIG. 18 is a flowchart showing a flow of the entire process including the relationship between the preliminary photographing, the analysis according to the first embodiment, the analysis according to the second embodiment, and the actual photographing, in the present disclosure.

First, a sample (slide, biological sample SPL) is set on the stage 11 of the fluorescent microscope 10 (step 501). The setting of a sample may be performed by a transporting robot or a manual operation.

Next, the stage control unit 31 moves the stage 11 to bring an appropriate place of the biological sample SPL close to the photographing range AR (step 502).

The movement of the stage 11 is the one type of movement of the stage 11 described in the first embodiment. In this step, the position of the stage 11 in the z-axis direction is located at the exposure start position $z_{start}$ of the divided photographing range Zscan_1.

Next, the stage control unit 31 and the image obtaining unit 32 act in synchronization to take a fluorescent image for adjusting a focal position (step 503).

This step is the preliminary photographing. The method of taking a fluorescent image for adjusting a focal position is the one described in the paragraph of [Regarding Method of Taking Fluorescent Image for Adjusting Focal Position] in the first embodiment.

Next, the distribution information calculation unit 33 analyzes the taken fluorescent image for adjusting a focal position (step 504).

The analysis includes a method of obtaining average brightness of fluorescent images and a method of obtaining the number of bright spots having a brightness value of a threshold value set in advance or more.

Here, in the method of obtaining the number of bright spots, the number of pixels brighter than the background value of the fluorescent image can be counted, instead of counting of the number of bright spots.

Next, the distribution information calculation unit 33 determines whether or not the average brightness or the number of bright spots obtained in step 504 is larger than the threshold value set in advance (step 505).

In the case where the number of bright spots is compared with the threshold value, the threshold value can be usually about 100, for example.

In the case where the average brightness or the number of bright spots is smaller than the threshold value set in advance (No in step 505), the distribution information calculation unit 33 determines that the cell density in the biological sample SPL is low, and performs the image matching on the locus of the individual bright spot, which is described in the first embodiment, to calculate the distribution information of the fluorescent marker (step 506).

In the case where the average brightness or the number of bright spots is larger than the threshold value set in advance (Yes in step 505), the distribution information calculation unit 33 determines that the cell density in the biological sample SPL is high, and performs the texture analysis of the entire fluorescent image, which will be described in a second embodiment, to calculate the distribution information of the fluorescent marker (step 507).

If the distribution information of the fluorescent marker is obtained in step 506 or 507, next, the stage control unit 31 moves the stage 11 in the z-axis direction so that the optimal focal position determined by the distribution information can be obtained (step 508).

Next, the image obtaining unit 32 performs the actual photographing (step 509).

The fluorescent image obtained by the actual photographing is analyzed by an observer such as a pathologist, and is used for diagnosis.

Next, the data processing unit 20 determines whether or not another photographing place exists (step 510).

In the case where a photographing place still exists (Yes in step 510), the process returns to step 502 and is continued. In the case where a photographing place does not exist (No in step 510), the process is finished.

Hereinabove, the flow of the entire process including the relationship between the preliminary photographing, the analysis according to the first embodiment, the analysis according to the second embodiment, and the actual photographing in the present disclosure has been overviewed.

[Regarding Principle of Regarding as Texture and Analyzing]

Now, reasons of being capable of analyzing the entire fluorescent image for adjusting a focal position obtained in the preliminary photographing will be described.

There exist two reasons, and the first reason is caused due to the characteristic shape embossed by the overlapped loci of a lot of bright spots in the fluorescent image for adjusting a focal position.

In the case where the cell density is high, the number of bright spots is large, and a lot of loci of bright spots are overlapped in the fluorescent image taken in the preliminary photographing, the image of a dark portion of the locus of a defocused bright spot is difficult to determine. Then, only the brightest part of the loci of bright spots including the focused image 60 can be determined in the image. Therefore, although the locus of a bright spot originally has a circular shape or a semicircular shape, only "the brightest and nearly straight portion BL of the loci of bright spots" is embossed in the fluorescent image as a determinable shape. In this embodiment, this is a principle for determination.

The second reason is the relative ratio of the thickness of the sample section being the range in which the fluorescent markers 55 are distributed, and the range for moving the focal position in the z-axis direction when the fluorescent image for adjusting a focal position is taken.

The thickness of the sample section fluorescence-stained is about 4 μm to 6 μm, and the bright spots of the fluorescent marker 55 distribute only in the range of the thickness. On the other hand, the range in which the focal position is moved in the z-axis direction when the fluorescent image for adjusting a focal position is taken is, for example, 20 μm to 50 μm.

As described above, the range in which the focal position is moved in the z-axis direction is several to ten times larger than the range in which the fluorescent marker 55 is distributed. In the case where the ratio is large, the position in the range in which the fluorescent marker 55 is distributed falls in a range of relatively small variability.

Therefore, the variability of the angle θ shown by "the brightest and nearly straight portion BL of the loci of bright spots" is considered to be small. Therefore, by analyzing the fluorescent image as texture and obtaining the average value of the angle θ shown by "the brightest and nearly straight portion BL of the loci of bright spots," it is possible to obtain an average height of the fluorescent marker 55 in the z-axis direction, i.e., the position in the z-axis direction at which a lot of bright spots are focused on.

Hereinabove, the principle of regarding the fluorescent image as texture and analyzing the texture has been described.

[Method of Obtaining Angle θ by Analyzing Texture (First)]

Next, a first method of obtaining the angle θ by analyzing texture will be described.

In this method, a plurality of directions for obtaining a frequency component with respect to the fluorescent image for adjusting a focal position obtained in the preliminary photographing are determined. Then, the frequency component in the determined direction is obtained, and the angle θ in the direction having the highest maximum frequency component is determined.

FIG. 19 is a diagram in which an x-axis direction being a horizontal direction of a fluorescent image, a y-axis direction being a vertical direction of the fluorescent image, and a direction A inclined by 45 degrees with respect to the x- and y-axis directions are determined as directions for obtaining a frequency component. As described above, the number of the directions for obtaining the frequency component is favorably three or more. The number of directions for obtaining the frequency component depends on the accuracy of the target angle θ.

The reason for this is that the direction of "the brightest and nearly straight portion BL of the loci of bright spots" is hard to be determined uniquely in the case of two directions. For example, as shown in FIG. 20, the cases where "the brightest and nearly straight portion BL of the loci of bright spots" appears in a direction of a pattern A and in a direction of a pattern B is considered. In order to distinguish the two directions and to determine the correct direction, two directions of the x-axis direction and the y-axis direction are insufficient.

By obtaining the frequency component of the fluorescent image including a lot of "the brightest and nearly straight portions BL of the loci of bright spots" in the direction determined as described above, it is possible to know in what direction many inclined angles of "the brightest and nearly straight portion BL of the loci of bright spots" are collected. This is because the direction vertically across "the brightest and nearly straight portion BL of the loci of bright spots" is a direction having the highest maximum frequency component.

For example, like the case of the loci of the bright spots of the fluorescent marker 55a shown in the case of Zscan_2 in FIG. 9, the assumption is made that the angle at the exposure start position $z_{start}$ is 0 degree, the angle at the exposure end position $z_{end}$ is 180 degrees, and the focused image 60 is positioned at the angle of 135 degrees.

In this case, the slope of "the brightest and nearly straight portion BL of the loci of bright spots" is same as that of a tangent at the position of the focused image 60 in the circle O, i.e. 45 degrees. Then, the direction vertically across "the brightest and nearly straight portion BL of the loci of bright spots" i.e., direction having the highest maximum frequency component is the direction A (−45 degrees direction). It can be seen that the angle θ is about 135 degrees from the relationship that the exposure start position $z_{start}$ is 0 degree and the exposure end position $z_{end}$ is 180 degrees.

Hereinabove, the first method of obtaining the angle θ by analyzing texture has been described.

[Method of Obtaining Angle θ by Analyzing Texture (Second)]

Next, a second method of obtaining the angle θ by analyzing texture will be described.

In this method, the fluorescent image 70 for adjusting a focal position obtained in the preliminary photographing is used as an original image, and images obtained by displacing the original image by a predetermined number of pixels to a predetermined direction are generated for a plurality of directions. Then, correlations between the generated plurality of images and the original image are obtained. The direction of the image having the lowest correlation is regarded as the direction vertically across "the brightest and nearly straight portion BL of the loci of bright spots," and the angle θ is determined.

Figure 21F:
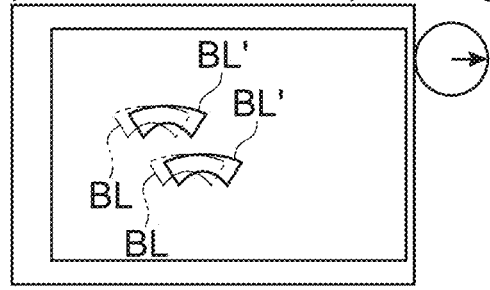
FIG. 21F is a diagram showing a state where a correlation between the original image and an image obtained by displacing the original image by the predetermined number of pixels to the right direction is obtained.

FIGS. 21 to 21E are each a diagram showing a state where a correlation between the original image and an image obtained by displacing the original image by the predetermined number of pixels to a predetermined direction is obtained. The second method will be described with reference to the drawings.

(1) First, the distribution information calculation unit 33 obtains the fluorescent image 70 for adjusting a focal position being the original image.

The original image is shown in the top left of FIG. 21, and two "brightest and nearly straight parts BL of the loci of bright spots" are photographed in the image. It should be noted that because the case where the cell density in the biological sample SPL is high is assumed in this embodiment, 100 or more "brightest and nearly straight parts BL of the loci of bright spots" are photographed in the original image actually. However, only two "brightest and nearly straight parts BL of the loci of bright spots" are shown to make FIG. 21 more clear.

(2) Next, the distribution information calculation unit 33 generates images obtained by displacing the original image by a predetermined number of pixels to a plurality of directions.

FIGS. 21A to 21E each show a state where the original image is displaced by every 45 degrees in a range from 0 to 180 degrees in five directions being the plurality of directions. In FIGS. 21A to 21E, the positions represented by dotted lines are the positions of "the brightest and nearly straight parts BL of the loci of bright spots" before the original image is displaced. By what angle and in which directions the original image is displaced depend on the accuracy of the target angle θ.

It should be noted that the predetermined number of pixels for displacing the image is usually about 15 pixels in the case where the width of "the brightest and nearly straight portion BL of the loci of bright spots" is 10 pixels, for example.

(3) Next, the distribution information calculation unit 33 calculates the correlation between the original image and images obtained by displacing the original image by a predetermined number of pixels.

Examples of the method of calculating the correlation include a method of comparing the difference for each pixel between the original image and the displaced image. The method is used for images in FIGS. 21A to 21E. In the images shown in FIGS. 21A and 21E, overlap between "the brightest and nearly straight portions BL of the loci of bright spots" and images BL' obtained by displacing "the brightest and nearly straight portions BL of the loci of bright spots" is large, and the difference is small. Specifically, the correlation is high.

On the other hand, in the image of FIG. 21C, almost no overlap between "the brightest and nearly straight portions BL of the loci of bright spots" and images BL' obtained by displacing "the brightest and nearly straight portions BL of the loci of bright spots" exists, and the difference is the largest. Specifically, the correlation is the lowest.

(4) Last, the distribution information calculation unit 33 determines the direction of the image having the lowest correlation as the direction vertically across "the brightest and nearly straight portion BL of the loci of bright spots," and obtains the angle θ.

In the image of FIG. 21C, because the original image is displaced to the downward direction, it can be seen that the direction of the angle of 90 degrees or 270 degrees is the direction vertically across "the brightest and nearly straight portion BL of the loci of bright spots." Therefore, if the angle at the exposure start position $z_{start}$ is 0 degree and the angle at the exposure end position $z_{end}$ is 180 degrees, the angle θ is about 90 degrees.

Hereinabove, the second method of obtaining the angle θ by analyzing texture has been described.

[Supplementary Note]

Embodiments of the present disclosure are not limited to the above-mentioned embodiments and various modifications can be made without departing from the gist of the present disclosure.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An image obtaining apparatus, comprising:
an image sensor configured to form an image;
an optical system configured to:
   apply excitation light from a light source to at least a partial area of a biological sample, the part including a fluorescent label, and
   cause the image sensor to form a fluorescent image of the partial area;
a movement control unit configured to
   move a focal position of the optical system to an optical axis direction of the optical system and a direction perpendicular to the optical axis;
a generation unit configured to:
   continuously expose the image sensor during the movement of the focal position of the optical system, and generate an image of the partial area; and
a calculation unit configured to
   analyze spatial frequency of the generated image, and
   calculate positional information in the optical axis direction of the fluorescent label by using at least results of the analysis,
   obtain moving images by moving the generated image by one or more pixels set in advance in one or more directions,
   obtain a correlation between the generated image and each of the obtained moving images, and
   determine one of the one or more directions of one of the obtained moving images having lowest correlation.

2. The image obtaining apparatus according to claim 1, wherein the calculation unit is configured to:
   analyze the spatial frequency of the generated image in at least one direction of the one or more directions, wherein the at least one direction is different from two directions set in advance, the two directions being perpendicular to each other,
   determine one of the directions, which has highest spatial frequency, and
   calculate the positional information based on the determined one of the directions.

3. The image obtaining apparatus according to claim 2, wherein the calculation unit is configured to
   store information of the obtained correlation and the positional information in advance, and
   calculate the positional information from the determined one of the directions based on the obtained information of the obtained correlation.

4. An image obtaining method, comprising:
generating excitation light causing a fluorescent label of a biological sample to emit light;
applying the generated excitation light to at least a partial area of the biological sample, the part including the fluorescent label, and causing an image sensor to form a fluorescent image of the partial area by an optical system;
moving a focal position of the optical system to an optical axis direction of the optical system and a direction perpendicular to the optical axis;
continuously exposing the image sensor during the movement of the focal position of the optical system, and generating an image of the partial area;
analyzing spatial frequency of the generated image, and calculating positional information in the optical axis direction of the fluorescent label by using at least results of the analysis;
obtaining moving images by moving the generated image by one or more pixels set in advance in one or more directions;
obtaining a correlation between the generated image and each of the obtained moving images, and
determining one of the one or more directions of the obtained moving images having lowest correlation.

5. An image obtaining method, comprising:
generating excitation light causing a fluorescent label of a biological sample to emit light;
applying the generated excitation light to at least a partial area of the biological sample, the part including the fluorescent label, and causing an image sensor to form a fluorescent image of the partial area by an optical system;
moving a focal position of the optical system to an optical axis direction of the optical system and a direction perpendicular to the optical axis;
continuously exposing the image sensor during the movement of the focal position of the optical system, and generating plurality of images of the partial area;
analyzing spatial frequency of each of the generated plurality of images to determine maximum spatial frequency,
comparing the determined maximum spatial frequency of each of the generated plurality of images with each other, and
selecting an image having the maximum spatial frequency from the generated plurality of images.

6. The image obtaining method according to claim 5, further comprising
analyzing an image of locus of a fluorescent marker in the selected image having the maximum spatial frequency to determine distribution information of the fluorescent marker.

7. The image obtaining method according to claim 6, wherein
the fluorescent marker is a bright spot of a predetermined color labeled on the biological sample.

8. The image obtaining method according to claim 7, further comprising
detecting the shape and number of fluorescent markers based on the color of each of the fluorescent markers.

* * * * *